(12) United States Patent
Watson et al.

(10) Patent No.: US 6,936,270 B2
(45) Date of Patent: Aug. 30, 2005

(54) DEVICE AND METHOD FOR TREATING CONDITIONS OF A JOINT

(75) Inventors: David A. Watson, Westwood, MA (US); Thomas J. Smith, Weston, MA (US); Richard Laporte, Waltham, MA (US); Jianbing Chen, Belmont, MA (US); Paul Ashton, Boston, MA (US)

(73) Assignee: Control Delivery Systems, Inc., Watertown, MA (US)

( * ) Notice: Subject to any disclaimer, the term of this patent is extended or adjusted under 35 U.S.C. 154(b) by 0 days.

(21) Appl. No.: 10/139,143

(22) Filed: May 2, 2002

(65) Prior Publication Data

US 2003/0139811 A1 Jul. 24, 2003

Related U.S. Application Data

(63) Continuation-in-part of application No. 09/985,319, filed on Nov. 2, 2001, now abandoned.
(60) Provisional application No. 60/291,606, filed on May 18, 2001, provisional application No. 60/255,157, filed on Dec. 14, 2000, and provisional application No. 60/245,184, filed on Nov. 3, 2000.

(51) Int. Cl.[7] .................................................. A61K 2/02
(52) U.S. Cl. ....................................................... 424/423
(58) Field of Search .......................................... 424/423

(56) References Cited

U.S. PATENT DOCUMENTS

| | | | |
|---|---|---|---|
| 5,902,598 | A | 5/1999 | Ashton et al. |
| 6,001,386 | A | 12/1999 | Ashton et al. |
| 6,051,576 | A | 4/2000 | Cynkowsk et al. |

FOREIGN PATENT DOCUMENTS

| | | | |
|---|---|---|---|
| EP | 0 911 025 | | 5/1999 |
| WO | WO9717032 A | * | 5/1997 |
| WO | WO00042929a | * | 7/2000 |

OTHER PUBLICATIONS

Illi et al: "stimulation of Fracture healing by Local Application of Humoral factors Integrated in Biodegradable Implants", European Journal of Pediatric Surgery: Official Journal of Austrian Association of Pediatric Surgery, Aug. 1998, vol. 8, No. 4.*

Bias, P. et al. Sustained–Release Dexamethasone Palmitate: Pharmacokinetics and Efficacy in Patients with Activated Inflammatory Osteoarthritis of the Knee. Clinical Drug Investigation 6, 429–436 (2001).

Brown, K. et al. A Novel Controlled–Release Intraarticular Delivery System. Arthritis and Rheumatism 9, S267 (Nov. 7, 1993).

Derendorf, H. et al. Aktuelle Rheumatologie. 15, 145–153 (1990)—[English Abstract].

* cited by examiner

Primary Examiner—Carlos A. Azpuru
(74) Attorney, Agent, or Firm—Ropes & Gray LLP

(57) ABSTRACT

A therapeutically effective compound is locally administered by associating the compound with a piece of orthopedic hardware that is implanted at an appropriate site within a body. The compound is adapted, such as through a sustained release device, to administer an effective dosage continuously over an extended period of time. The compound may be administered, for example, to a joint of a mammal by intraarticularly implanting a sustained release device to deliver the therapeutically effective compound within a synovial capsule of the joint, such that synovial fluid concentration of the compound is greater than plasma concentration of the compound. A wide range of orthopedic hardware, such as bone screws and staples, may be adapted to use in the systems described herein to provide treatment for a variety of medical conditions.

39 Claims, 19 Drawing Sheets

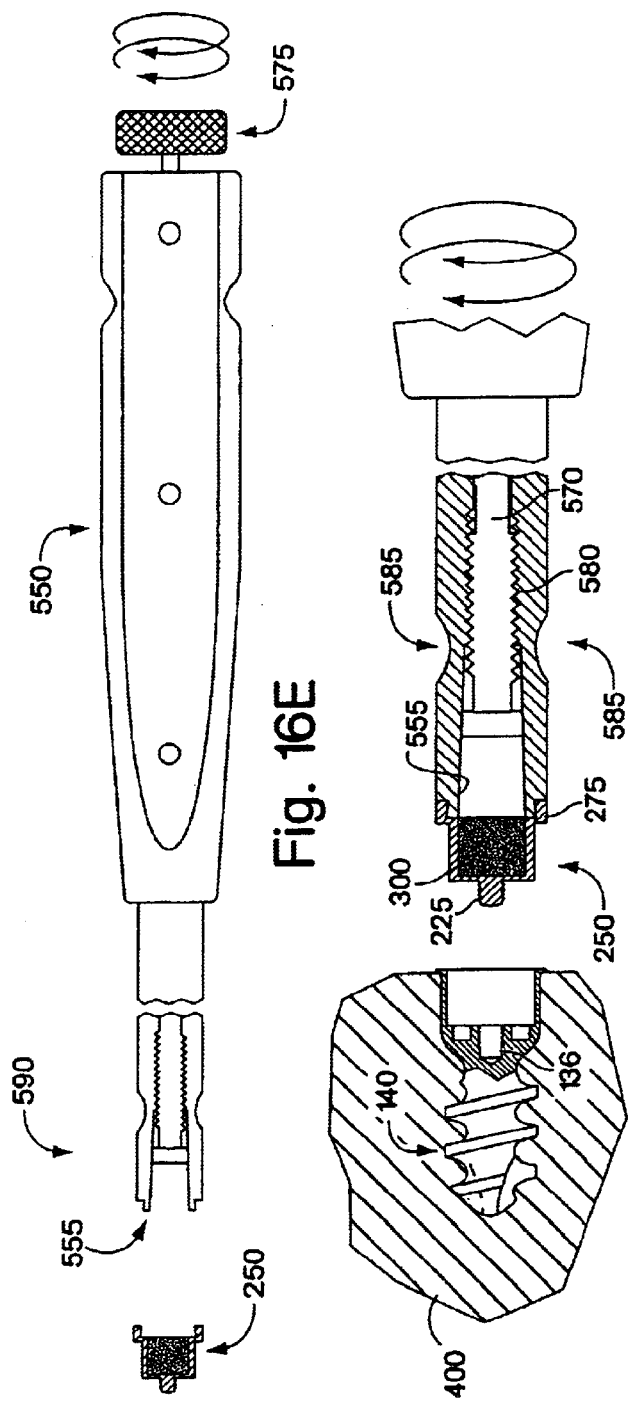
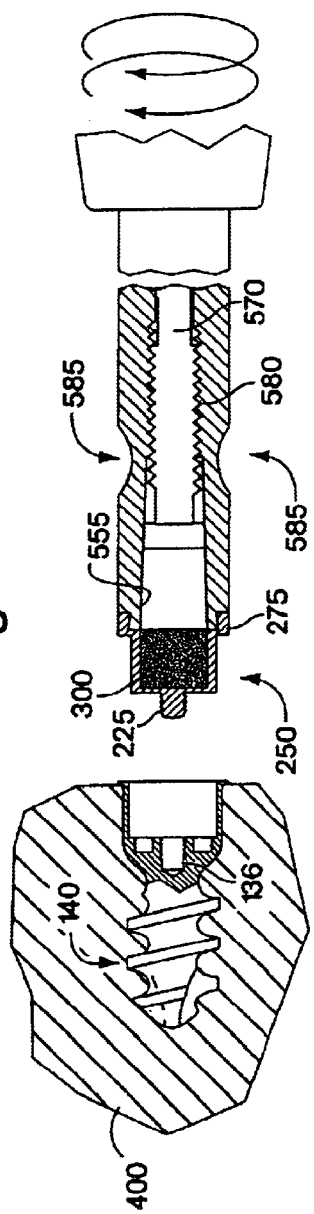
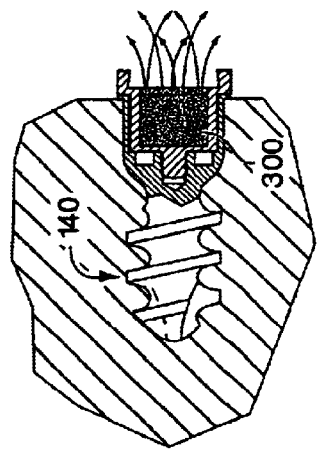
Fig. 16E
Fig. 16F
Fig. 16G

DEVICE AND METHOD FOR TREATING CONDITIONS OF A JOINT

CROSS REFERENCE TO RELATED APPLICATIONS

This application is a continuation-in-part of U.S. patent application Ser. No. 09/985,319, filed on Nov. 2, 2001, now abandoned which claimed the benefit of U.S. Prov. Pat. App. No. 60/291,606, filed on May 18, 2001, U.S. Prov. Pat. App. No. 60/255,157, filed on Dec. 14, 2000, and U.S. Prov. Pat. App. No. 60/245,184, filed on Nov. 3, 2000. The specifications of each of the above-referenced applications are incorporated herein by reference.

BACKGROUND OF INVENTION

Pain, in and of itself, constitutes a sufficient impetus for remedial action. Moreover, otherwise productive individuals lose more time due to pains, particularly in the joints, than to any other cause. Civilization and technological advances have ushered in a relatively sedentary existence, both as to work environment and leisure activities, which increases the likelihood of such pain-causing ailments. Although the term is applied to a wide variety of disorders, arthritis generally denotes the inflammation of a joint whether as a result of a disease, an infection, a genetic defect or some other cause. The long term effects of arthritis range from chronic pain to crippling disability.

Osteoarthritis is a disease that attacks cartilage. Surfaces of joint cartilage and underlying bone compress and become irregular, leading to pain, inflammation, bone spurs and limited movement. Osteoarthritis is one of the most common disabilities in the United States, affecting over 15% of the population. As osteoarthritis progresses, serious joint damage and chronic pain can result. Treatment alternatives are limited and, in many cases, ineffective. Aside from weight reduction and avoiding excessive stress on the joint cartilage, there is currently no specific treatment to halt cartilage degeneration or to repair damaged cartilage caused by osteoarthritis. The goal of treatment is to reduce joint pain and inflammation while improving and maintaining joint function. Current pharmacological treatments include oral anti-inflammatory and anti-pain medications. The effectiveness of these treatments decreases as the disease progresses. In severe osteoarthritis, joint replacement surgery is common. Sometimes surgery is forestalled with injections of steroids into the affected joint, but the delivery of drugs in this manner is painful, and the drugs themselves provide decreasing effectiveness and wear off after several weeks. In 1999, there were over 500,000 joint replacement surgeries funded by Medicare in the United States, which were likely mainly due to osteoarthritis.

Severe arthritis involves a serious auto-immune reaction for which steroids theoretically provide treatment. The efficacy of steroids, however, is compromised by the systemic toxicity resulting from the dosage required to penetrate the natural barriers of the joints and the need for repeated treatments due to the chronic nature of the disease.

Steroids can be administered in different ways. For example, they can be orally ingested as tablets, or by injected into a muscle or into a vein.

Steroid injections are a common treatment for a variety of conditions in which inflammation causes pain, swelling and other problems. Joint pain due to osteoarthritis and rheumatoid arthritis are examples of conditions for which steroid injections may be helpful. Injections have the advantage of placing the steroids, often glucocorticoids, for example, directly into a painful area. Because of this, steroid injections are able to reduce inflammation and pain relatively quickly. Unfortunately, steroid injections must be administered by a medical doctor, are sometimes accompanied by an anesthetic to numb the area to be injected, and typically last for only several months before a second injection is required. Furthermore, the injected area may become more painful over the first 24 hours after the local anaesthetic wears off, requiring application of a cold compress or painkillers. In addition, it is usually suggested that the joint be rested for 24–48 hours after the injection, especially for weight-bearing joints such as the knee. Immediately after injection, the concentration of steroid within the joint is maximal. The injection, however, becomes progressively less effective however as the steroid clears the joint. Repeated injections to maintain therapeutic drug concentrations are not clinically acceptable, yet high initial doses carry a risk of toxicity. It is difficult to maintain therapeutic drug concentrations.

Common side effects associated with steroid treatment include weight gain, thinning of the bones (osteoporosis), easy bruising, indigestion, mood changes, rises in blood sugar and blood pressure, and increased likelihood of developing infections. Because of their long-term side effects, it is recommended that corticosterolds should be given only after a careful and usually prolonged trial of less hazardous drugs. Furthermore, severe rebound follows the withdrawal of corticosterolds in active diseases, in part due to the down regulation of naturally occurring glucocorticoid steroids.

Intraarticular injections of corticosteroids may temporarily help control local synovitis in one or two particularly painful joints. Triamcinolone hexacetonide may suppress inflammation for the longest time; other depot corticosteroids, including prednisolone tertiary-butylacetate, also are effective. The soluble 21-phosphate preparations of prednisolone or dexamethasone are not recommended because of rapid clearance from the joint and very short duration of action. Side effects may not be as pronounced when steroids are given by injection to the knee. However, the effects of a steroid injection to the knee typically is limited to several months before another injection is required. Also, injections provide an initial level of steroid that is greater than therapeutically required and which rapidly declines beneath therapeutic levels.

Cytotoxic/immunosuppresive compounds (e.g., methotrexate, cyclosporine) are increasingly used for severe, active rheumatoid arthritis. They can suppress inflammation and may allow reduction of corticosteroid doses. Yet, major side effects can occur, including liver disease, pneumonitis, and bone marrow suppression. Thus, patients require careful supervision by a specialist.

Broadly, there exists a need for an improved implantable sustained release drug delivery device and method and apparatus for implantation of said device. In particular, there exists a need for an improved device and method for treating conditions of joint or bones, such as arthritis, without undesirable systemic side effects and a need for repeated injections.

SUMMARY OF INVENTION

A therapeutically effective compound is locally administered by associating the compound with a piece of orthopedic hardware that is implanted at an appropriate site within a body. The compound is adapted, such as through a sustained release device, to administer an effective dosage continuously over an extended period of time. The compound may be administered, for example, to a joint of a mammal by intraarticularly implanting a sustained release device to deliver the therapeutically effective compound within a synovial capsule of the joint, such that synovial fluid concentration of the compound is greater than plasma concentration of the compound. A wide range of orthopedic hardware, such as bone screws and staples, may be adapted to use in the systems described herein to provide treatment for a variety of medical conditions.

BRIEF DESCRIPTION OF DRAWINGS

By way of example only, embodiments of the present invention will be described with reference to the accompanying drawings, in which.

14A–14D illustrate various cross-sectional views of aspects of a drug delivery system according to the embodiments of the present invention represented in FIGS. 12A–12D and/or 13A–13B.

Figure 15A:
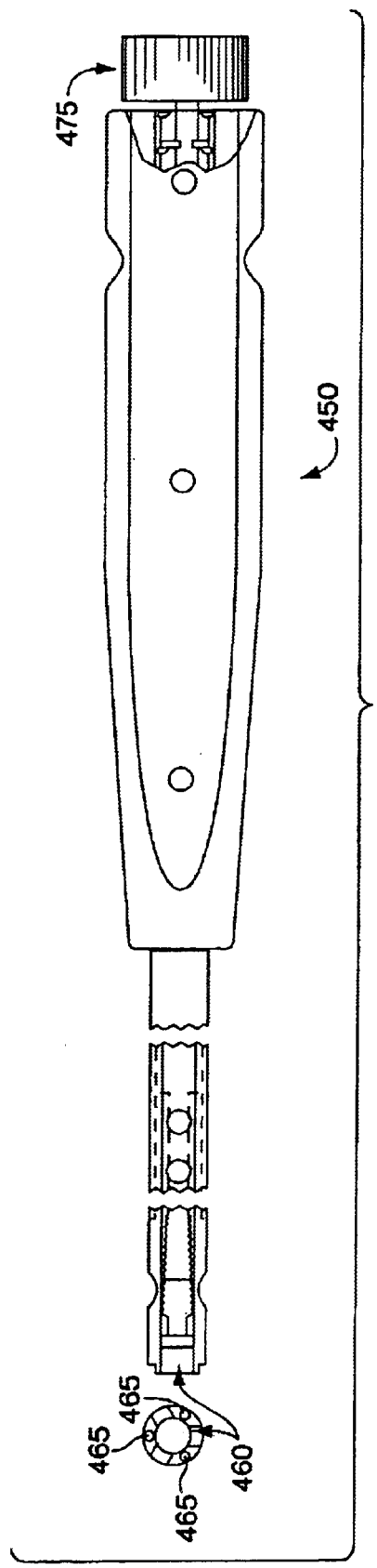
Figure 15B:
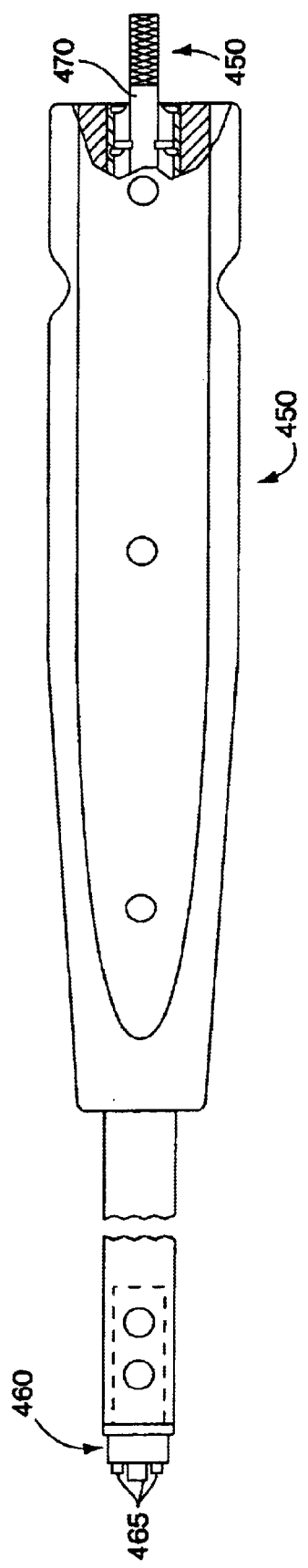

FIGS. 15A–15B illustrate an apparatus used to insert a drug delivery device in accord with the invention.

FIGS. 16A–16G illustrate a method of inserting a drug delivery device in accord with the invention.

DETAILED DESCRIPTION

In one embodiment, the present invention provides a method for administering a therapeutically effective compound to the synovial fluid of a joint. The method comprises the step of implanting a sustained release device within the joint such that the therapeutically effective compound is released within the synovial capsule. The synovial fluid concentration of the compound remains greater than plasma concentration for the lifetime of the sustained release device.

In one aspect of the invention, the synovial fluid concentration of the compound remains at least one order of magnitude greater than the plasma concentration. In a preferred aspect of the invention, the synovial fluid concentration of the compound remains several orders of magnitude greater than the plasma concentration.

Additional applications of the systems described herein will become readily apparent to those skilled in the art from the following detailed description, wherein various embodiments of the invention are described simply by way of illustrating the best mode contemplated of carrying out the invention. As will be realized, the invention is capable of other and different embodiments, and its details are capable of modifications in various obvious respects, all without departing from the invention. For example, the aspects of the invention presented herein are similarly applicable to other medical applications, including but not limited to bone fixation and localized treatments for adjacent bone masses. Accordingly, the description is to be regarded as illustrative and not as restrictive.

The present invention is particularly effective in treating Joint diseases, such as inflammatory joint diseases, e.g., various forms of arthritis. Examples of inflammatory joint diseases that can be effectively treated in accordance with embodiments of the present invention include arthritis associated with spondylitis, diffuse connective tissue diseases such as rheumatoid arthritis, infectious arthritis and osteoarthritis. Rheumatoid arthritis is almost exclusively an inflammatory disease, while osteoarthritis is a degenerative one, which may have secondary inflammatory components. Osteoarthritis may be more generally characterized as a complex of interactive degradative and reparative processes in cartilage and bone, with secondary inflammatory changes, particularly in the synovium. In either case treatment may be effectively administered directly to the appropriate site using the systems described herein.

Various therapeutically effective compounds can be deployed with the systems described herein including, for example, glucocorticoid anti-inflammatories such as dexamethasone, fluocinolone, cortisone, prednisolone, flumetholone, and derivatives thereof, as well as, non-steroidal anti-inflammatory drugs and immune suppressants such as cyclosporines, and antibiotics, cartilage protectants and disease modfying agents, such as chondroitin sulfate, enzyme inhibitors, and/or antisense compounds such as antisense oligonucleotides.

As employed throughout this disclosure, the expression, "sustained release device" is intended to mean a device that is capable of releasing one or more drugs and/or compounds over an extended period of time in a controlled fashion. The drugs or compounds may advantageously include, but are not limited to, a steroid, an anti-inflammatory drug, an antibiotic, an anti-viral agent, a cancer-fighting drug, including antiproliferative, antimyotic, and antimetabolite compounds, or a pain reliving drug. Examples of sustained release devices useful in the present invention may be found in, for example, U.S. Pat. Nos. 6,051,576, 5,773,019, 6,001, 386, 5,902,598, and 5,378,475 (incorporated herein by reference, in their entireties). Suitable sustained release devices could comprise an inner core bearing an effective amount of at least one low-solubility agent and at least one non-bioerodible polymer coating layer that is permeable to the low-solubility agent(s).

Suitable low-solubility agents may include, but are not limited to, corticosteroids such as dexamethasone and triamcinolone acetonide, angiostatic steroids such as anecortave acetate, antibiotics including ciprofloxacin, non-steroidal anti-inflammatory agents such as indomethacin and flurbiprofen, co-drugs including low-solubility co-drugs of salts or conjugates of synergistic pharmacological agents such as suramin/amiloride or 5-FU/THS, and combinations thereof. Standard pharmaceutical textbooks, such as *Remington's Pharmaceutical Sciences* (Mack Publishing Company, Easton, Pa. 1985), provide procedures to obtain a low-solubility form of a drug.

As used herein, the term "low-solubility" is intended to mean a solubility less than about 10 mg of compound per 1 ml (of water at a temperature of 25° C. as measured by procedures set forth in the 1995 USP). This includes compounds that are slightly soluble, from about 10 mg/ml to about 1 mg/ml, very slightly insoluble, from about 1 mg/ml to about 0.1 mg/ml, and practically insoluble or insoluble compounds less than about 0.1 mg/ml.

As used herein, the terms "compound" and "drug" are intended to refer to any of the above-mentioned biologics, drugs and/or compounds, as well as any other drugs, compounds, or other substances, in any useful combination, for obtaining a therapeutic effect by delivery through the sustained release devices described herein, unless a different meaning is explicitly indicated.

Embodiments of the present invention include the sustained release of two or more drugs simultaneously. The sustained release device may be configured to provide release of a compound to synovial fluid such that the synovial fluid concentration remains greater than plasma concentration. The sustained release device is designed to maintain an optimal dosage level at the target site over the entire duration of treatment without substantial variability in dosing over time.

The sustained release device may be surgically implanted intraarticularly, i.e., within the synovial joint. In embodiments of the present invention, the sustained release device may be configured for attachment to a bone, as in co-pending U.S. Provisional Patent Application Serial Nos. 60/245,184 and 60/291,606, the entire disclosures of which are incorporated by reference herein. In other embodiments, the sustained release device may be configured for attachment to soft tissue, such as a ligament or a tendon, with suturing.

The concentration of the compound in the synovial fluid may remain greater than the plasma concentration of the compound during the lifetime of the device. As the compound is released from the device, it may enter the synovial fluid. Over time a steady state condition is established where the rate of compound entering the synovial fluid is substantially equivalent to the rate of compound eliminated from the joint. The compound that is eliminated from the joint is then distributed throughout the rest of the body and is eliminated via excretion. This redistribution and excretion establishes the differential levels between the synovial fluid and the plasma. In embodiments of the present invention, the plasma concentration of the compound remains at or below 5 ng/ml. At such low concentrations, adverse systemic side effects are unlikely to develop. In contrast, the synovial fluid concentrations remain substantially therapeutic, during release of the compound from the sustained release device. The exact concentration depends on the condition and therapeutic index of the compound.

Sustained release of the therapeutically effective compound may be provided for a duration of about 3 months to about 10 years, such as from about 6 months to about 5 years. In embodiments of the system, sustained release of the therapeutically effective compound is provided for about 3 years. As such, the need for frequent, repeated administrations, such as with injections, is avoided.

The following examples are merely illustrative of the present invention and they should not be considered as limiting the scope of the invention in any way, as these examples and other equivalents thereof will become more apparent to those skilled in the art in light of the present disclosure.

Twelve Month Single Dose Toxicity Study in Beagle Dogs

Animals

| Species: | Canis familiaris |
|---|---|
| Strain: | Beagle |
| Source: | Covance |
| Age at Initiation: | 5–9 months |
| Weight at Initiation: | 10–12 kg, to be documented in the study file |
| Number of Males (including spares): | 6 + 1 spare |

Experimental Methodology

Study Design

| Group Number | Number of Animals Males | Device | Dosing Regimen | Euthanasia |
|---|---|---|---|---|
| 1 | 3 | Fluocinolone acetonide implant | 1 implant in each hindlimb joint | 1/group at Day 29, 91, and 365 |
| 2 | 3 | Fluocinolone acetonide implant | 4 implants in each hindlimb joint | |

Frequency and Duration of Administration

Devices were administered once via bilateral intraarticular implants. The day of surgical implantation was Day 1.

Implants

The devices were made as follows. Fluocinolone acetonide, USP, was compressed into 1.5 mm diameter tablets using standard pharmaceutical methods. The tablets were placed into preformed cups made from silicone elastomer. Cup size was dependent on dosage form. These cups were attached to polyvinyl acetate (PVA) suture tabs. For the 2 mg implants, the surface of the tablet not coated with silicone was attached to a suture tab with PVA solution. For the 6 mg implant, a side of the silicone cup was attached perpendicular to the suture tab. Finally, the assemblies were dip coated with PVA.

The implants were then cured at 135° C. for 5 hours and placed within the primary package. The product in the primary package was placed in a self-adhesive pouch and sterilized using gamma irradiation.

Pre-operative Procedures

Anesthesia and Antibiotic Therapy

The animals were preanesthetized with atropine (0.4 mg/kg IM) and acepromazine (0.1 mg/kg IM). After about 10–30 minutes, the animals were initially anesthetized with methohexital INa at 10–15 mg/kg IV, to effect. The animals were immediately intubated and maintained in anesthesia with isoflurane inhalant anesthetic delivered through a volume-regulated respirator. The $ETCO_2$ was maintained within individual physiological ranges. An intravenous drip of lactated Ringer's solution was begun at a rate of approximately 1.0 ml/kg/hr. Procaine/Benzathine penicillin (40,000 IU/kg, IM) was also given.

Surgical Preparation

Hair was removed from the entire leg. Any excess hair was removed by vacuum. The surgical site was prepared for aseptic surgery by first washing the leg with povidone-iodine scrub solution followed by an application of 70% isopropyl alcohol, which was allowed to dry. Dura-Prep™ or similar solution was then applied to the entire leg and also allowed to dry. The entire leg, including the foot, was appropriately draped for strict aseptic surgery.

Surgical Procedures

Surgery was performed on both knee joints of all animals. A lateral skin incision was made to expose the fascia lata overlying the vastus lateralis cranially and the biceps fernoris caudally. The joint was exposed through an incision in the lateral intermuscular septum to expose the femur by anterior retraction of the vastus lateralis and posterior retraction of the biceps femoris. Care was taken not to disrupt the tendon of origin of the long digital extensor as it originates from the lateral femoral condyle. The joint capsule was opened, the patella luxated medially, and the joint was held in full flexion. 2 mg devices were placed in the right leg and 18 mg implants were placed in the left leg. The implants were placed within the anterior intercondyloid fossa, immediately lateral to the origin of the posterior cruciate ligament. The bone may be slightly deepened at this location with a curette to accept the implant. The implant was sutured in place to the posterior cruciate ligament. The joint capsule was closed with 3/0 PDS in a simple interrupted fashion. The retinaculum and intermuscular septum were closed with 2/0 Vicryl in a continuous pattern. The fascia lata were closed with 2/0 PDS, and the subcutaneous tissues with 3/0 PDS, both in a simple continuous pattern. The skin was closed with 3/0 Vicryl in a subcuticular pattern.

Blood Collection

Blood was collected from a peripheral vessel. Blood volumes represent whole blood and are approximate amounts.

| Timepoint | Clinical Pathology Hematology | BAC Clinical Chemistry | Coagulation | Cortisol | Blood | Synovial Fluid |
|---|---|---|---|---|---|---|
| Days 3, 7, 21, 29, 91, and 365 | X | X | X | X | X | X |
| Volume of Whole Blood/Timepoint | 1.3 ml | 1.8 ml | 1.8 ml | 1.8 ml | 5.0 ml | 0.3–0.5 ml |
| Anticoagulant | EDTA | None | Sodium Citrate | None | EDTA | EDTA |

The blood samples were processed for plasma, the plasma was extracted, and the plasma was placed immediately in a ≦−70°C. freezer until transferred for analysis.

Synovial Fluid

After anesthesia (acepromazine, 0.2 mg/kg. IM followed by sodium pentobarbital, 22 mg/kg, IV, to effect), an attempt was made to obtain synovial fluid. Syriovial fluid samples were immediately stored at ≦−70° C. in polypropylene tubes until transferred.

TABLE 1

Assayed Concentrations (ng/ml) of Fluocinolone Acetonide in Dog Plasma Samples

| Time (Days) | Dog 1001 | Dog 1002 | Dog 2001 | Dog 2002 | Dog 3001 | Dog 3002 |
|---|---|---|---|---|---|---|
| 3 | 1.89 | BQL | BQL | BQL | BQL | BQL |
| 7 | BQL | BQL | BQL | BQL | 16.9 | BQL |
| 21 | 0.57 | BQL | BQL | BQL | 4.92 | BQL |
| 29 | BQL | BQL | BQL | BQL | BQL | BQL |

TABLE 2

Assayed Concentrations (ng/ml) of Fluocinolone Acetonide in Dog Synovial Fluid Samples (Left Leg)

| Time (Days) | Dog 1001 | Dog 1002 | Dog 2001 | Dog 2002 | Dog 3001 | Dog 3002 |
|---|---|---|---|---|---|---|
| 3 | 656 | 357 | 89.0 | 193 | 788 | 207 |
| 7 | 290 | 405 | 194 | 279 | 35300 | 251 |
| 21 | 1070 | 373 | X | 393 | 5180 | 276 |
| 29 | 457 | 379 | 57.8 | 956 | X | 210 |
| 56 | 202071 | 541 | X | X | 36.9 | X |

BQL = Below Quantition Limit, 5 ng/ml;
X = No sample collected for this timepoint

TABLE 3

Assayed Concentrations (ng/ml) of Fluocinolone Acetonide in Dog Synovial Fluid Samples (Right Leg)

| Time (Days) | Dog 1001 | Dog 1002 | Dog 2001 | Dog 2002 | Dog 3001 | Dog 3002 |
|---|---|---|---|---|---|---|
| 3 | 52.0 | 36.6 | 600 | 24.4 | 57.9 | 40.7 |
| 7 | 62.4 | BQL | 98.4 | 47.7 | 171 | 8.30 |
| 21 | 7.27 | BQL | BQL | 144 | 51.5 | BQL |
| 29 | BQL | BQL | BQL | BQL | 16.4 | 7.86 |

TABLE 3-continued

Assayed Concentrations (ng/ml) of Fluocinolone Acetonide in Dog Synovial Fluid Samples (Right Leg)

| Time (Days) | Dog 1001 | Dog 1002 | Dog 2001 | Dog 2002 | Dog 3001 | Dog 3002 |
|---|---|---|---|---|---|---|
| 56 | 19.3 | BQL | X | X | X | BQL |

BQL = Below Quantition Limit, 5 ng/ml;
X = No sample collected for this timepoint The results shown in Tables 1–3 demonstrate the effectiveness of one use of the systems described herein.

Phamacokinetic Study of a Fluocinolone Acetonide Implant in the Stifle Joint of Sheep Animals

| Species: | *Ovis aries* (Sheep) |
|---|---|
| Strain: | Rambouillet |
| Source: | K Bar Livestock |
| Age at Initiation: | Adult |
| Weight at time of surgery/treatment: | 35–75 kg |

-continued

| Number and Sex: | 12 males + 1 spare |
| --- | --- |
| | 12 females (nonpregnant) + 1 spare |

Experimental Methodology

The objective of this study was to determine both the local and systemic pharmacokinetic profile of an intra-articular fluocinolone acetonide (FA screw) implant in the stifle joint of sheep. This study group consisted of 24 animals randomized into 2 groups of 6 males and 6 females per group, as shown in Table 4. The animals underwent surgical implantation of the FA Screw test device in the stifle joint on Day 1. Following a recovery period, blood and synovial fluid were collected periodically for pharmacokinetic determination. Following completion of a 24 month observation period, the animals were euthanized and subjected to necropsy.

TABLE 4

Study Design

| Group Number | Number of Animals Males | Test Device Females | Dosage Level* | Dosing Regimen | Euthanasia/ Necropsy Day |
| --- | --- | --- | --- | --- | --- |
| 1 | 6 | 6 | FA Screw | 1 implant | Surgical implantation of test device in one stifle joint | 24 months after implantatic |
| 2 | 6 | 6 | | 3 implants | | |

*Each implant nominally delivers approximately 60 micrograms/day of fluocinolone acetonid Frequency and Duration of Administration Devices were administered once via surgical implantation on Day 1.

Implants

The implant was a polymer-coated, sustained-release delivery system for Fluocinolone Acetonide (FA). The implant contained 55 mg of FA and was designed to deliver the drug for approximately 3 years. The tablet core contained approximately 55 mg of FA granulated with 10% PVA. The tablet core was positioned and adhered via an adhesive, such as a silicone adhesive, in the interchangeable head of the bone screw. The overall device geometry was that of a cancellous bone screw (i.e. the base) in which the head of the screw has been hollowed out to accept a removable cup (i.e. the payload) containing the drug tablet. In this embodiment, the screw was approximately $^{11}/_{16}$" in length and is no more than ¼" at its widest point (i.e. the screw head), The payload was sized to fit into the screw and to accommodate the tablet.

Preoperative Procedures

Anesthesia and Antibiotic Therapy

ProBios® or the equivalent (15 grams per os) was administered prior to surgery and on Day 2. The animals were premedicated with glycopyrrolate (0.02 mg/kg, intramuscularly [IM], butorphanol (0.05 mg/kg, intravenously [IV]), and diazepamr (0.2 mg/kg IV). Intravenous indwelling catheters were placed in peripheral veins as needed. Anesthesia was induced with methohexital (~10 mg/kg, IV). The animal was intubated and maintained in anesthesia with Halothane® inhalant anesthetic delivered through a volume regulated respirator, started as soon as possible after intubation. An esophageal tube was also placed into the rumen to aid in keeping it decompressed. Lactated Ringer's solution was administered intravenously at a rate of ~10 ml/kg/hour. The total volume of crystalloid fluids administered did not exceed 2 L. Antibiotic prophylaxis began prior to surgery with the use of Cefotaxime (50 mg/kg, IV or IM).

Surgical Preparation

Eye ointment was applied to the eyes and all fleece was clipped from the entire leg, with any excess fleece removed by vacuum. The animal was positioned in lateral recumbency and the surgical site prepared for aseptic surgery by first washing the area with povidone-iodine scrub solution and 70% isopropyl alcohol, which was allowed to dry. Then, Dura-Prep™ or a similar solution was applied to the area and also allowed to dry. The area was then appropriately draped for strict aseptic surgery.

Surgical Procedures

A lateral skin incision was made to expose the fascia lata overlying the vastus lateralis cranially and the biceps femoris caudally. The joint was exposed through an incision in the lateral intermuscular septum to expose the femur by anterior retraction of the vastus lateralis and posterior retraction of the biceps femoris. Care was taken not to disrupt the tendon of origin of the long digital extensor as it originates from the lateral femoral condyle. The lateral geniculate vessels may be cauterized during this procedure. The joint capsule was opened, the patella luxated medially, and the joint held in full flexion. The appropriate number of implants (1 for Group 1; 3 for Group 2) were placed either within the anterior intercondyloid fossa (immediately lateral to the origin of the posterior cruciate ligament), the suprapatellar fossa, or the medial femoral condyle. The joint capsule was closed with 2/0 PDS in a simple interrupted, fashion. The retinaculum, intermuscular septum, and fascia lata were closed with #2 PDS or Prolene® in a continuous pattern. The subcutaneous tissues were closed with 2/0 PDS and the skin closed with staples.

Blood Collection

Blood was collected from a peripheral vessel. Blood volumes represent whole blood and are approximate amounts.

Sample Collection Schedule

| Timepoint | Clinical Pathology Hematology | Bioanalytical Chemistry Serum Chemistry | Blood | Synovial Fluid |
| --- | --- | --- | --- | --- |
| Prior to surgery | X | X | | |
| On Day 7 | | | X | X |
| Once monthly for Months 1–12 | | | X | X |
| Once quarterly for Months 13–24 | | | X | X |
| Prior to necropsy | X | X | X | X |
| Volume of Whole Blood/Timepoint | 0.5 ml | 1.8 ml | 5.0 ml | 0.3–0.5 ml |
| Anticoagulant | EDTA | None | EDTA | EDTA |

The bioanalytical chemistry (BAC) blood samples were processed for plasma, and the plasma was extracted and stored at $\leq -70°$ C. until transferred for analysis.

Synovial Fluid

After anesthesia, an attempt was made to obtain synovial fluid. Synovial fluid samples were stored at $\leq -70°$ C. until transferred. Anesthesia for synovial fluid collection began after a minimum 12 hour fast (maximum 24 hours). An IM injection of diazepam (0.5 mg/kg) was given and then an IV catheter placed, followed by IV injections of 0.035 mg/kg xylazlne and 3.0 mg/kg ketamine (combined in a syringe and injected slowly). Additional ketamine was given as needed in increments of approximately 1 mg/kg. This anesthesia may be reversed with IV injections of yohimbine (0.125 mg/kg) or atipamezole (10 μg/kg).

Figure 1:
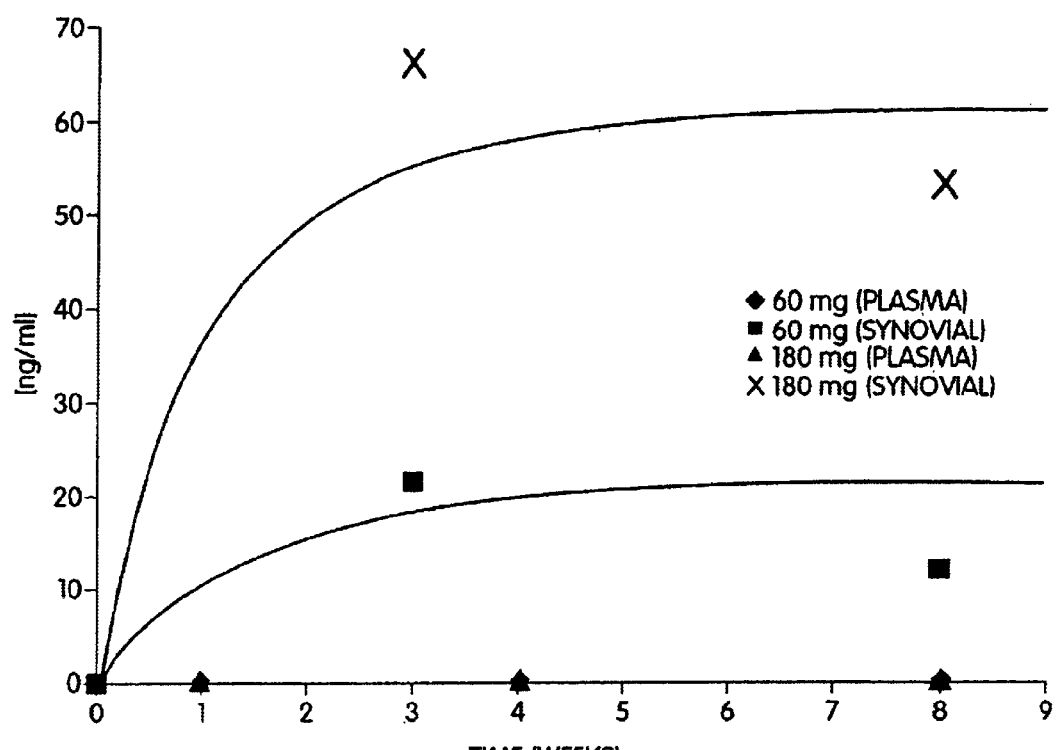
FIG. 1 shows a graph of fluocinolone acetonide (FA) in plasma versus synovial fluid in sheep in accord to one aspect of the invention.

FIG. 1 depicts the measured plasma versus synovial fluid concentrations in sheep and illustrates both the local and systemic pharmacokinetic profiles of intra-articular fluocinolone acetonide implants in the stifle joint of sheep. FIG. 1 represents a three-fold increase in FA concentrations in the synovial fluid of sheep at three and eight weeks. Plasma levels are between 0–0.35 ng/ml reflecting that drug delivered within the joint capsule is maintained at a high level over long periods of time. This differential in plasma and synovial fluid demonstrate the value of local therapy in treating joint disease. These results are illustrative of the general efficacy of the method and apparatus of the invention, but are not to be construed as limiting the scope of the invention in any way.

Figure 2A:
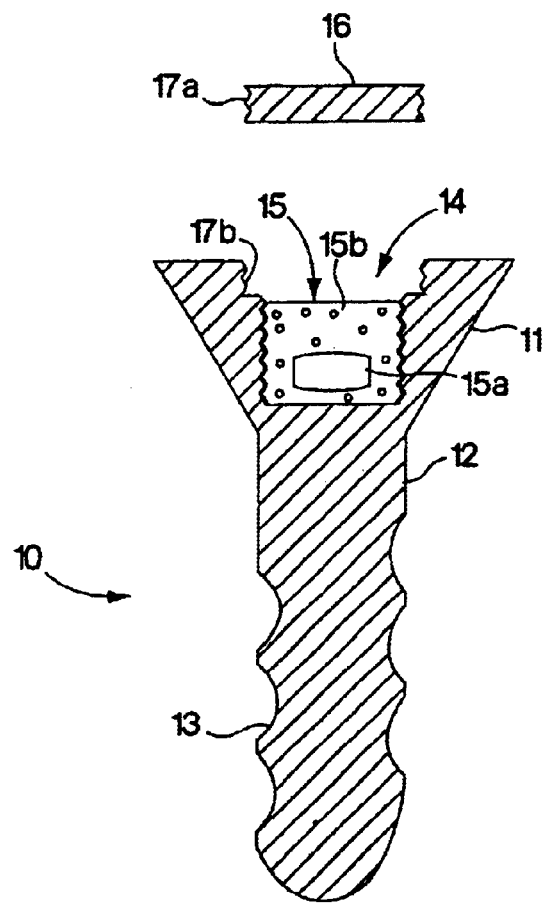
FIGS. 2A and 2B respectively show an exploded cross-sectional view of a drug delivery system according to an embodiment of the present invention and a top view of a removable attachable retainer according to an embodiment of the present invention.
Figure 2B:
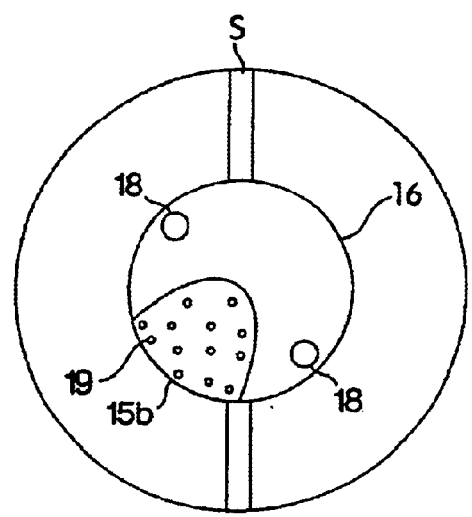

In one aspect, the fluocinolone acetonide, USP, may be compressed into tablets using standard pharmaceutical methods and dip coated with PVA, as discussed above, although other conventional processing means for applying the PVA (or other type of polymer coating or rate-limiting diffusion membrane) are acceptable. Instead of placing the tablets into preformed silicone elastomer cups, however, the tablets may be disposed within a bone screw 10 or other type of implantable device, as illustrated for example, in FIG. 2A and other figures appended hereto, which are described in greater detail below. A drug delivery system 10 according to one aspect of the present invention is depicted in FIGS. 2A and 2B. The drug delivery system 10 (hereinafter "system 10") is generally in the form of a hollow-headed screw for attaching a sustained release device to a bone. System 10 comprises a hollow head 11, a neck 12, and a threaded shank 13 for threading system 10 into a hole in a bone. Head 11 is configured to allow system 10 to be screwed into a bone with head 11 substantially flush with the bone; for example, it can be chamfered and include slots S as shown in FIG. 2B to accommodate a wrench or other device engaging and rotating the system 10. Device 10 is made of a material suitable for long-term insertion in the body, such as conventional surgical stainless steel. System 10 further comprises a chamber 14, such as a cylindrical chamber, formed inside head 11, for holding a sustained release device 15. While the system 10 will be described in further detail below, it will be understood that the following description is only one example embodiment, and that the following description is not intended in any way to limit the scope of the claims.

Sustained release device 15 includes an inner core 15a comprising an effective amount of a low-solubility agent and a non-bioerodible polymer coating layer 15b that is permeable to the low-solubility agent, wherein polymer coating layer 15b covers inner core 15a and is essentially non-release rate limiting. The polymer coating layer preferably covers the inner core and is essentially non-release rate limiting. In another aspect, the inner core may be substantially covered by the non-bioerodible polymer coating layer 15b that is not permeable to the low-solubility agent, but instead defines and provides a plurality of small openings therein to permit sustained interaction between the inner core 15a and an external environment.

In still another aspect of the invention, the sustained release device 15 may be formed from a bioerodible material bearing a drug or a plurality of drugs. Bioerodible, as used herein, includes bioresorbable and bioabsorbable materials, as well as strictly bioerodible materials. Technically, bioabsorbable or bioresorbable materials are completely metabolized and eliminated from the body, whereas bioerodible materials are not necessary completely broken down and eliminated. Suitable bioerodible (and/or resorbable) polymeric materials include linear aliphatic polyesters (polyglycolide, lactide, caprolactone, hydroxybutyrate) and their copolymers (poly-[glycolide-lactide], [glycolide-caprolactone], [glycolide-trimethylene carbonate], [lactic acid-lysine], [lactide-urethane], [ester-amide]), polyanhydrides, poly(orthoesters), polyphosphazenes, orthoesters, and poly(orthoester)/poly(ethylene glycol) block copolymers, to name a few. The bioerodible material may comprise combinations of materials or layers to achieve a desired result of bioeroding or bioabsorbing at a known, controlled rate.

Referring to FIGS. 2A and 2B, system 10 further comprises a removably attachable retainer 16, as of stainless steel, for retaining sustained release device 15 in chamber 14. Retainer 16 is generally cylindrical and comprises threads 17 a in its outer wall for threadingly engaging threads 17b in an inner wall of chamber 14. Retainer 16 further comprises holes 18 for mating with torque transmitting pins of a screwdriver to remove and attach retainer 16 to system 10, and one or more openings 19 for allowing the drug from inner core 15a of sustained release device 15 to escape system 10. Those skilled in the art will understand that retainer 16 can be removably attached to system 10 by methods other than threads 17a, 17b.

Figure 5:
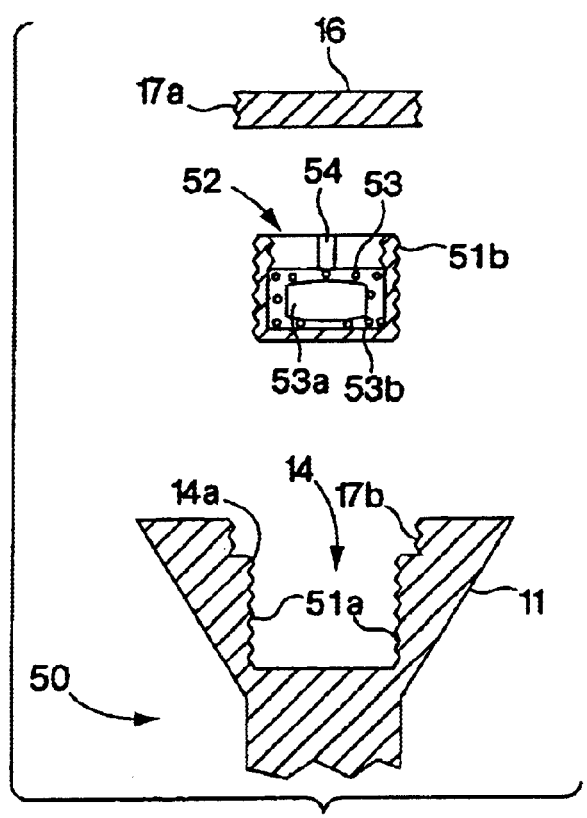
FIG. 5 shows an exploded cross-sectional view of a drug delivery system according to a further embodiment of the present invention.

In another embodiment of the present invention, shown in FIG. 5, a system 50 identical to that shown in FIGS. 2A and 2B is provided, except that an inner surface 14a of chamber 14 has threads 51a, and a second chamber 52 is removably attachable inside chamber 14. Second chamber 52 carries a sustained release device 53 comprising an inner core 53a and a polymer coating layer 53b, functionally similar to sustained release device 15 described in detail above. Second chamber 52 has threads 51b that threadingly engage threads 51a in the inner wall of chamber 14 to attach second chamber 52 to first chamber 14, and a pair of slots 54 for engaging a tool, such as a screwdriver, to screw second chamber 52 in and out of first chamber 14. After second chamber 52 is attached to chamber 14, retainer 16 is installed as described above.

Figure 3:
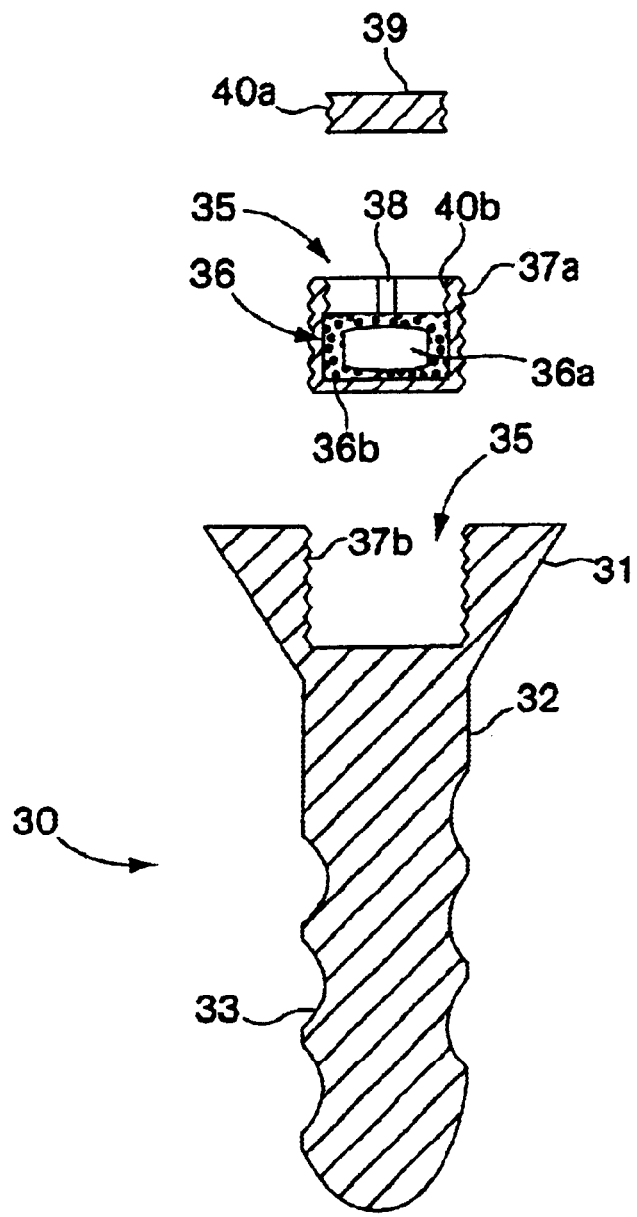
FIG. 3 shows an exploded cross-sectional view of a drug delivery system according to a further embodiment of the present invention.

In another embodiment of the present invention, shown in FIG. 3, system 30 comprises a hollow head 31, neck 32, threaded shank 33 for threading system 30 into a hole in a bone, and a first chamber 34 in head 31, similar to system 10 described above. However, in this embodiment of the present invention, a second chamber 35 is removably attachable inside first chamber 34, and carries a sustained release device 36 comprising an inner core 36a and a polymer coating layer 36b, functionally similar to sustained release device 15 described in detail above. Second chamber 35 has threads 37a that threadedly engage threads 37b in the inner wall of first chamber 34 to attach second chamber 35 to first chamber 34, and a pair of slots 38 for engaging a tool, such as a screwdriver, to screw second chamber 35 in and out of first chamber 34.

Figure 4:
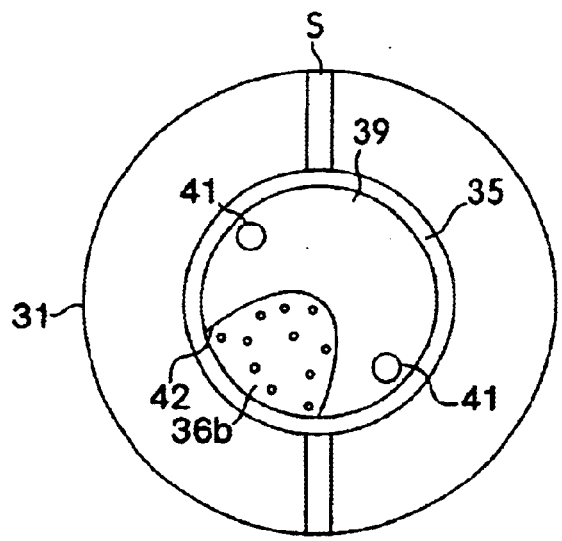
FIG. 4 shows a top view of a removable attachable retainer according to the embodiment of the present invention shown in FIG. 3.

Referring now to FIGS. 3 and 4, system 30 further comprises a removably attachable retainer 39, as of stainless steel, for retaining sustained release device 36 in second chamber 35. Retainer 39 is generally cylindrical and comprises threads 40a in its outer wall for threadingly engaging threads 40b in an inner wall of second chamber 35. Retainer 39 further comprises holes 41 for mating with a screwdriver to remove and attach it to second chamber 35, and one or more openings 42 for allowing the drug from inner core 36a of sustained release device 36 to escape system 30. Those skilled in the art will understand that retainer 39 can be removably attached to second chamber 35 by methods other than threads 40a, 40.

To attach the system of the embodiments of the present invention shown in FIGS. 2A–5 to a body, such as a human body, a hole, such as but not limited to a chamfered hole, may be first drilled into a bone. The assembled system 10, 30, 50 is then screwed into the hole such that the head of the device is flush with the bone. The sustained release device 15 or second chamber 35, 52 containing the sustained release device can be easily replaced as necessary when the drug of the inner core 15a, 36a, 53a has been completely released without removing the entire system from the body.

Figure 6:
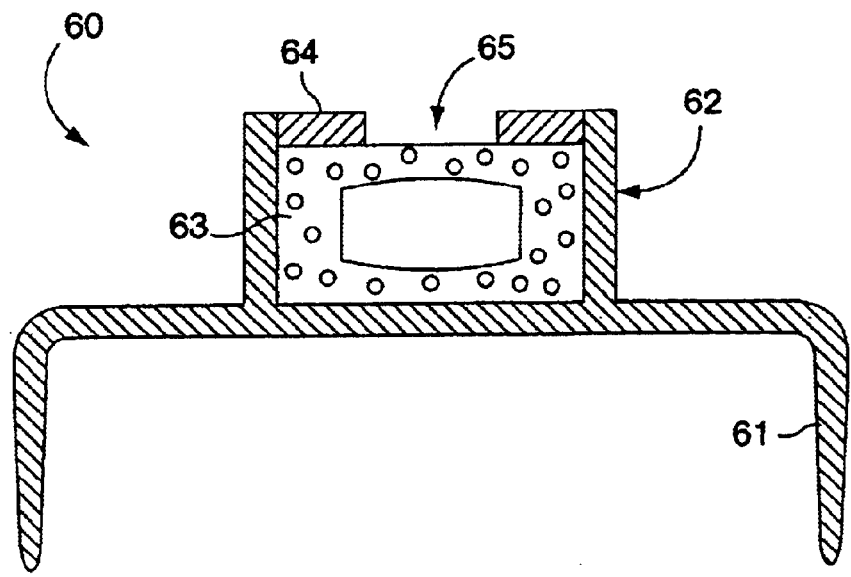
FIG. 6 shows a cross-sectional view of a drug delivery system according to a further embodiment of the present invention.
Figure 7:
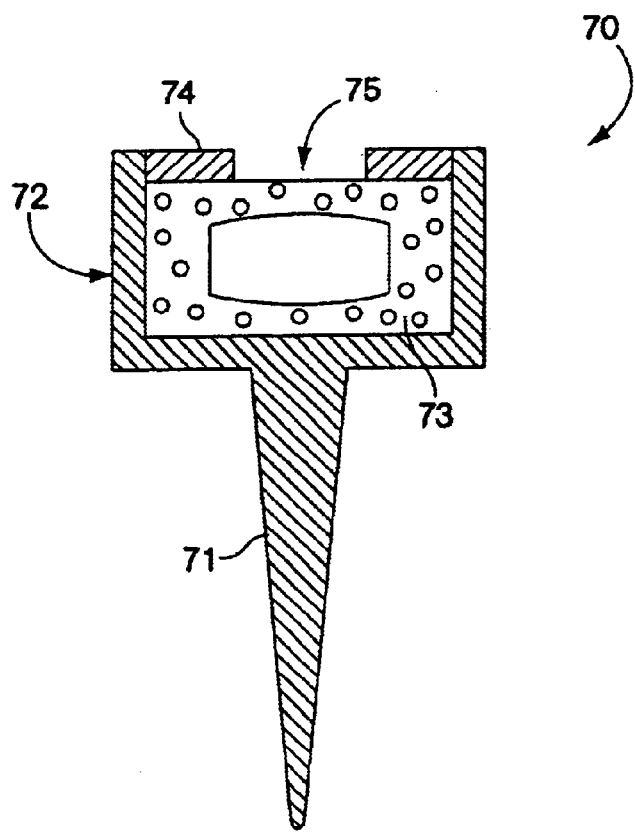
FIG. 7 shows a cross-sectional view of a drug delivery system according to a further embodiment of the present invention.

In other embodiments of the present invention, illustrated in FIGS. 6 and 7, the system 60, 70 comprises a staple 61 or a nail 71 that is driven into the bone instead of a screw. Still further, the system 60 illustrated in FIG. 6 may be configured to clasp around a body part, such as a bone, by deformation of the outwardly protruding portions of staple 61 until a suitable securement of the staple 61 to the body part is obtained. A chamber 62, 72 holds a sustained release device 63, 73, which is retained in chamber 62, 72 by a removably attachable retainer 64, 74 having a hole 65, 75 for allowing release of the drug. Of course, in the embodiments of FIGS. 6 and 7, the system 60, 70 does not sit flush with the bone, but protrudes somewhat. To minimize irritation to surrounding soft tissue, the sharply angled edges may be chamfered or rounded.

Figure 8:
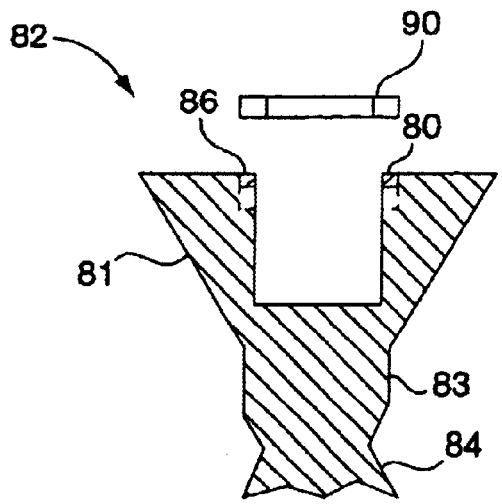
FIG. 8 shows a cross-sectional view of a drug delivery system according to yet another embodiment of the present invention.
Figure 9A:
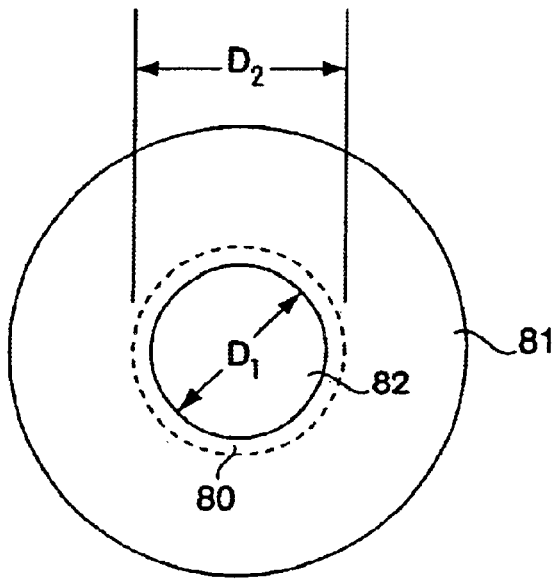
FIGS. 9A–9C depict top views of the drug delivery system depicted in FIG. 8.
Figure 9B:
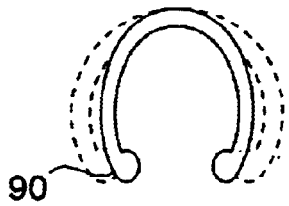
Figure 9C:
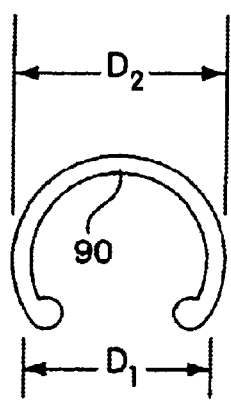

In still another embodiment of the invention, as shown in FIG. 8, a groove 80 is provided in a head 81 of system 85. As depicted, the system comprises a head 81 having a chamber 82, a neck 83, and a threaded shank 84 for threading device 85 into a bone or into a hole formed in a bone. Groove 80 is formed within the head 81 to have an outer diameter $D_2$ greater than the diameter $D_1$ of the chamber and is set apart from the top surface of the head 81 so as to be bounded by a retaining ledge 86 on an upper portion thereof. A retaining member 88 is removably insertable within groove 80, as shown in FIGS. 9A–9C. FIG. 9A shows another aspect of the relation between groove 80 and chamber 82. In this embodiment, it is preferred that the retaining member 88 possess a curvilinear shape, such as a c-shape, as shown in FIG. 9A, wherein at least a portion of the member has a diameter substantially equal to $D_2$ and at least a portion having an inner diameter less than $D_1$. Further, it is desired that this retaining member 88 be at least sufficiently resilient to permit elastic deformation of at least a portion thereof to permit insertion of the retaining member into groove 80.

In an equilibrium state, shown in FIG. 9C, the curvilinear member could not be inserted into the groove as it would be blocked by the retaining ledge 86 disposed on an upper side of the groove, retaining ledge possessing a diameter substantially similar to that of chamber 82. By appropriately disposed tensile or compressive forces, however, curvilinear member 88 may be sufficiently elastically deformed from the equilibrium position, depicted by dashed lines in FIG. 9A, to permit insertion into groove 80. In the inserted position, the retaining member 88 resumes its equilibrium position and an outer edge thereof abuts or conforms to the groove outer diameter. Moreover, at least a portion of an inner diameter of the retaining member possesses a diameter less than the diameter $D_1$ of the chamber 82, thus at least partially occluding the opening to the chamber. In this way, an object in the chamber, such as a sustained release device 53, may be retained within the chamber 82 by the portion of the retaining member 88 at least partially occluding the chamber. This occluding portion may comprise, as shown in FIG. 9C, a curvilinear portion which bounds an inner diameter $D_1$ of the chamber along an arc substantially equal to a length of the retaining member 88 or may simply comprise one or more projecting portions. Additionally, the degree of occlusion, or blocking of the chamber opening, may be varied in accord with the application by corresponding variation of the inner diameter of the occluding portion or projection portions of the retaining ring 88.

Figure 10A:
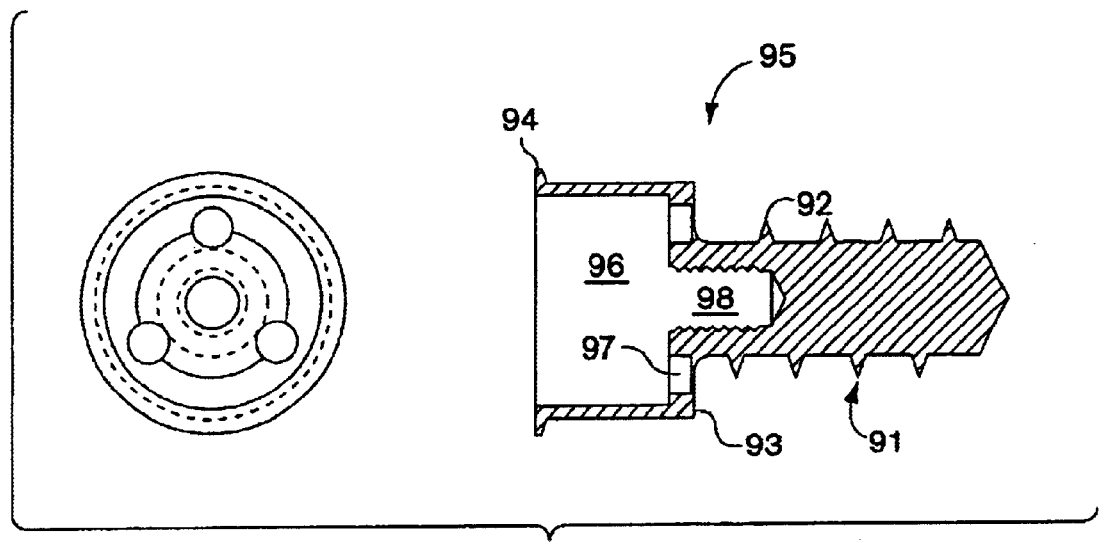
FIGS. 10A–10C depict cross-sectional views of a drug delivery system according to an embodiment of the present invention.
Figure 10B:
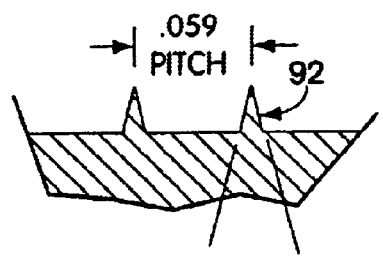
Figure 10C:
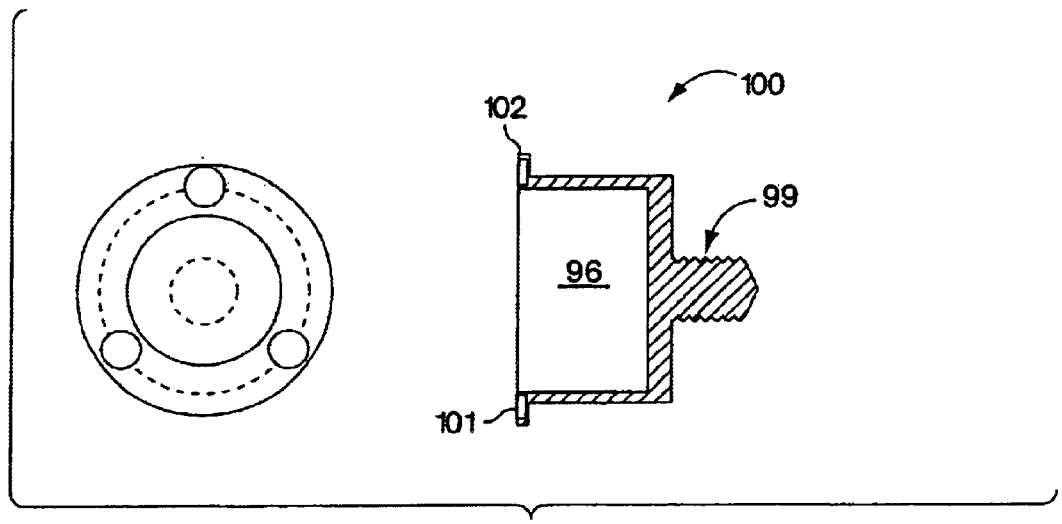

Still another embodiment of the invention is shown in FIGS. 10A–10C. FIG. 10A depicts a top view and a cross-sectional view of a screw 95 having a screw head defining a hollow head 96 therein. A sustained release holding device 100 (see FIG. 10C) is detachably insertable into the hollow-head 96 portion of screw 95 to retain and locally deliver a drug provided therein. Screw 95 includes a threaded shank 91 for threading the screw comprising the drug delivery system into a hole in a bone (not shown). It is generally preferred to position a top surface of the screw 95 substantially flush with the bone, by means of an appropriate screw configuration or by provision of appropriate burr holes. In this embodiment, an inside diameter of the hollow head 96 is 0.244 inches and an outer diameter of the hollow head is 0.264 inches. A lip 94 formed at a top portion of the hollow head 96 has an outer diameter of 0.295 inches.

The depth of the hollow head 96 is 0.154 inches and a plurality of torque transmitting structures 97 are provided in a base portion 93 of the hollow head to facilitate mechanical securement of the screw into a receiving surface, such as a bone. These torque transmitting structures 97, as illustrated in FIG. 10A comprise three Phillips-head receiving portions disposed along a diameter of about 0.172 inches to a depth of less than about 0.025 inches. A diameter of the torque transmitting structures 97 may be about 0.048 inches. In accord with previous aspects of the invention, this torque transmitting structure may comprise one or more slots or may comprise other structures conventionally employed to transmit torques. The threaded shank 91 is at least 0.32 inches in length and possesses, in the illustrated embodiment, a thread 92 having a pitch of 0.69 inches, a root (or minor) diameter of 0.125 inches, and a major diameter of 0.177 inches, wherein the sides of the threads intersect one another at a 30° angle. A tip of the threaded shank 91 is angled, such as at a 300° angle to facilitate insertion.

Formed within an upper portion of the threaded shank 91 exposed to the hollow head 96 is a recessed threaded portion 98 having a depth of about 0.18 inches. As shown in FIG. 10A, the minimum thread depth is approximately 0.110 inches with a thread major diameter of about 0.0595 inches. FIG. 10C illustrates the corresponding threaded shank 99 of the sustained release holding device 100. The sustained release holding device 100 is configured for insertion into the hollow head 96 of screw 95. As such, the outer diameter of the sustained release holding device 100 is 0.236 inches and the depth is approximately 0.170 inches. The inner diameter of the sustained release holding device 100 is 0.183 inches. At an upper portion thereof is a lip 102 having an outer diameter of 0.295 inches configured to matingly engage the lip 94 of the hollow head 96 of screw 95.

A plurality of torque transmitting structures 101 are provided in lip 102 to facilitate mechanical securement of the sustained release holding device 100 into the hollow head 96 of screw 95. These torque transmitting structures 97, as illustrated in FIG. 10C, comprise three Phillips-head receiving portions disposed along a diameter of about 0.236 inches to a depth of between about 0.15 inches. A diameter of the torque transmitting structures 97 may be about 0.048 inches. In accord with previous aspects of the invention, this torque transmitting structure may comprise one or more slots or may comprise other, structures conventionally employed to transmit torques. Projecting from a bottom portion of the sustained release holding device 100 is threaded shank 99, which is configured to matingly engage the recessed threaded portion 98 of the upper portion of the thread shank 91. In the illustrated embodiment, the threaded shank 99 has a length of about 0.10 inches and the threads extend along the shank about 0.06 inches.

Figure 11A:
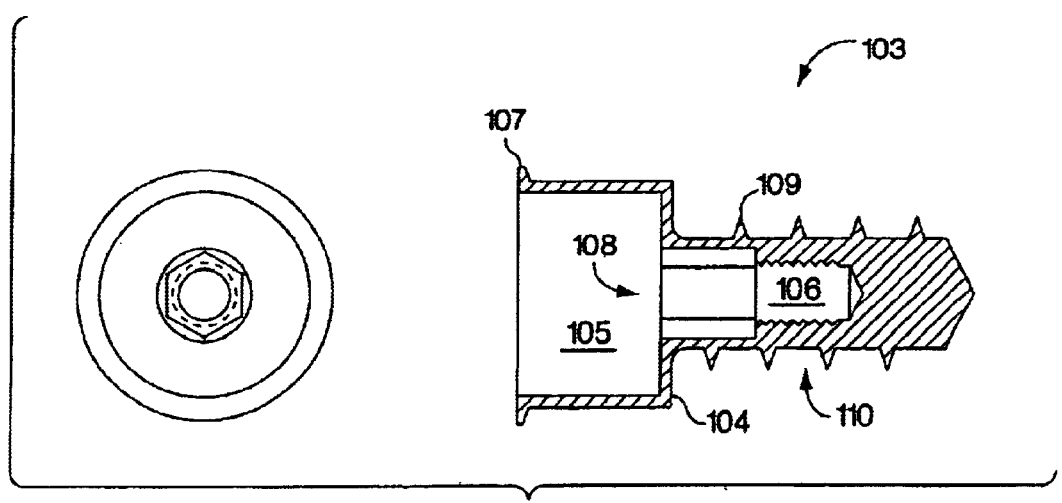
FIGS. 11A–11B depict cross-sectional views of another drug delivery system according to an embodiment of the present invention.
Figure 11B:
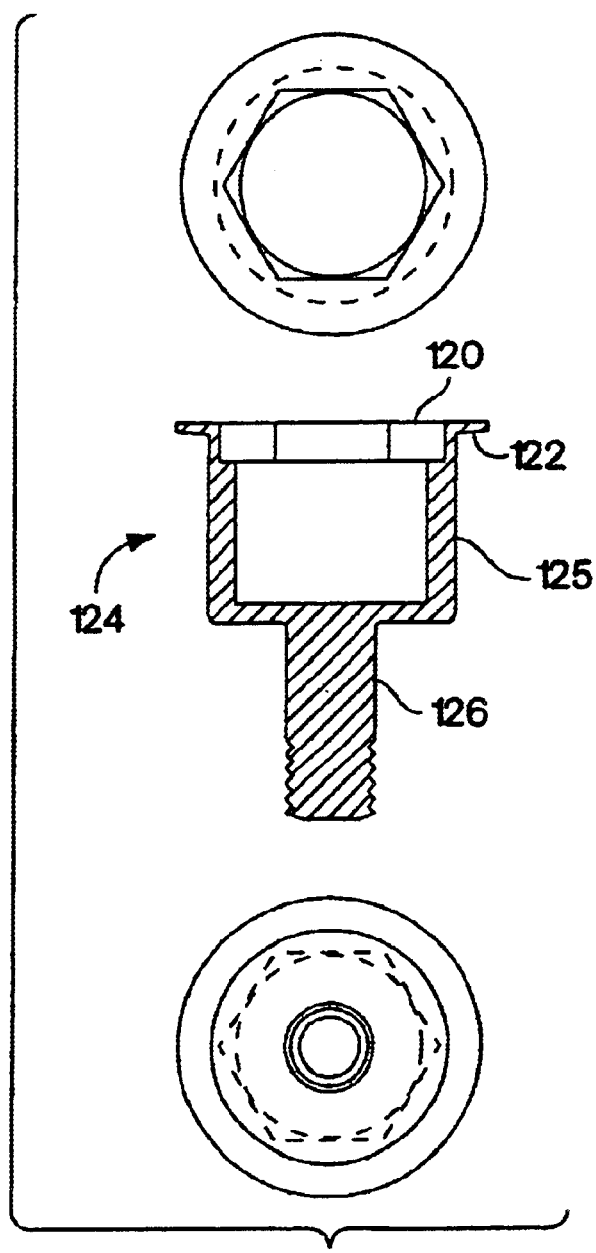

Yet another embodiment of the present invention is shown in FIGS. 11A–11B. FIG. 11A depicts a top view and a cross-sectional view of a screw 103 having a screw head defining a hollow head therein (i.e., a hollow head) 105. A sustained release holding device 124 (see FIG. 11B) is detachably insertable within the hollow-head 105 to retain and locally deliver a drug provided therein. Screw 103 also includes a threaded shank 110 for threading the screw 103 comprising the drug delivery system into a bone (not shown). It is generally preferred to position a top surface of the screw 103 substantially flush with the bone, by means of an appropriate screw configuration or by provision of appropriate burr holes.

In this embodiment, similar to the embodiment depicted in FIGS. 10A–10C, an inside diameter of the hollow head 105 is 0.244 inches and an outer diameter of the hollow head is 0.264 inches. Lip 107 formed at a top portion of the hollow head 105 has an outer diameter of 0.295 inches. The threaded shank 110 is about 0.37 inches in length and possesses, in the illustrated embodiment, a thread 109 having a pitch of 0.69 inches, a root (or minor) diameter of 0.125 inches, and a major diameter of 0.177 inches, wherein the sides of the threads intersect one another at a 3030° gle. A tip of the threaded shank 110 is angled, in the illustrated embodiment, at a 3030° le to facilitate insertion.

The interior depth of the hollow head 105 is 0.154 inches. Threaded shank 110 is provided on a bottom portion 104 of the hollow head 105. Formed within an upper portion of the threaded shank 110 and exposed to the hollow head 105 through a torque transmitting structure 108 is a recessed threaded portion 106 having a maximum depth of about 0.28 inches. As shown in FIG. 11A, the minimum thread depth of the threaded portion 106 is about 0.09 inches with a thread major diameter of about 0.0595 inches. Torque transmitting structure 108 is centrally provided in the base portion 110 of the hollow head 105 to facilitate mechanical securement of the screw 103 into a receiving surface, such as a bone. The torque transmitting structure 108 illustrated in FIG. 11A comprises a hexagonal key having a diameter of about 0.093 inches and a depth of about 0.125 inches.

FIG. 11B illustrates an embodiment of a sustained release holding device 124 configured for insertion into the hollow head 105 of screw 103. At a bottom portion of the sustained release holding device 124 is a threaded shank 126 corresponding substantially to the opening formed by the torque transmitting structure 108 and recessed threaded portion 106 of screw 103. The threaded shank 126 has a total axial length of about 0.20 inches, of which the threads comprise about 0.085 inches. The threads are configured to matingly engage those of the threaded portion 106 of screw 103 and are not provided in the portion of the threaded shank 126 corresponding to the screw 103 hexagonal key 108.

An outer diameter of the sustained release holding device 124 of FIG. 11B is 0.236 inches and the depth is approximately 0.184 inches. The inner diameter of the sustained release holding device 124 is 0.183 inches. At an upper portion thereof is a lip 122 having an outer diameter of 0.295 inches configured to matingly engage the lip 107 of the hollow head 105 of screw 103. A torque transmitting structures 120 is provided in lip 122 and/or hollow cylindrical body 125 of the sustained release holding device 124 to facilitate mechanical securement of the sustained release holding device 124 into the hollow head 105 of screw 103. The torque transmitting structure 120 illustrated in FIG. 11B comprises a hexagonal key having a diameter of about 0.1870 inches and a depth of about 0.040 inches.

Figure 12A:
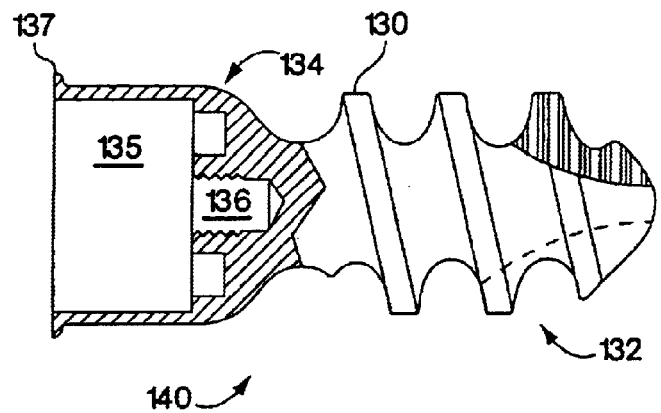
FIGS. 12A–12F depict cross-sectional views of a drug delivery system according to another embodiment of the present invention.

FIG. 12A is a cross-sectional view of a self-tapping or self-drilling screw 140 in accord with the invention having a screw head defining a hollow head 135 therein. A sustained release holding device 150. (see FIG. 12F) is detachably insertable within the hollow head 135 to retain and locally deliver a drug provided therein. Screw 140 also includes a threaded shank 132 for threading the screw 140 comprising the drug delivery system into a bone. It is generally preferred to position a top surface of the screw 140 substantially flush with the bone, by means of an appropriate screw configuration or by provision of appropriate burr holes. It is preferred, but not necessary, to round or chamfer the transition between the hollow head 135 and the threaded shank 132 to form a shoulder 134. In one aspect thereof, the shoulder 134 is rounded with a radius of 0.09 inches in the transition from the hollow head 135 to a point of inflection in concavity toward a middle portion of the shoulder 134, at which point the shoulder is rounded with a radius of 0.04 inches.

It is preferred that the screw 140 is made of a cleaned and passivated 6AL–4V titanium alloy, although any other surgical grade material of comparable strength, such as but not limited to stainless steel, composites, plastics, and/or ceramics exhibiting sufficient strength and/or hardness to permit insertion into and retention within the selected substrate (e.g., bone). To minimize stresses on the screw 140 and threaded shank 132, a pilot hole may be drilled into the bone.

Corners of the threaded shank 132 are rounded, to about 0.005 inches, to remove sharp corners. Further, all burrs from manufacture are to be removed and all edges are rounded to a minimum of about 0.003–0.005 inches. This may be accomplished, for example, by micro bead blasting with S2 bead or by any other conventional surface treatment methods known to those skilled in the art. Further, it is to be understood that the dimensions described and depicted with respect to the illustrated embodiment are not limiting as to any other embodiments of the invention and do not represent, for simplicity of illustration, conventional manufacturing tolerances.

In this embodiment, an inside diameter of the hollow head 135 is 0.244 inches and an outer diameter of the hollow head is 0.264 inches. Lip 137 formed at a top portion of the hollow head 135 has an outer diameter of 0.295 inches. The threaded shank 132 is about 0.39 to 0.41 inches in length and possesses, in the illustrated embodiment, a thread 138 having a pitch of about 0.111 inches and a root (or minor) diameter of about 0.125 inches at the tip of the screw 140, although the geometry of the tip may vary in a manner known to those skilled in the art in accord with the entry or initial drilling conditions expected for a particular application. In the embodiment depicted in FIG. 12D, the root diameter increases, from the initial root diameter of about 0.125 inches at the tip of the screw 140, by about 0.005 inch per thread up to about 0.135 inches at a base of the thread 138 adjacent the head of the screw. The thread 138 has a major diameter of about 0.250 inches and possesses a thread angle of about 15 15°=30 30° As illustrated, the threaded shank 132 has 9 threads per inch. A tip of the threaded shank 132 is smoothly angled, in the illustrated embodiment, at a 45 45° e and is radiused at about 0.062 inches.

Figure 12B:
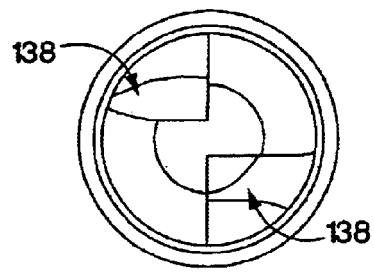
Figure 12C:
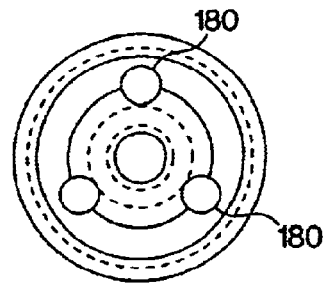
Figure 12D:
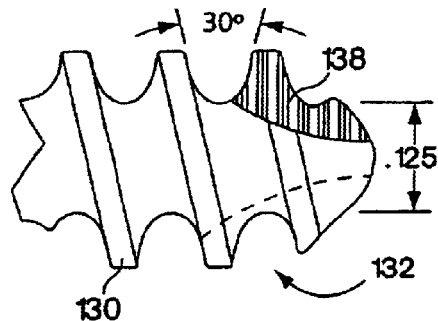

With respect to the cutting faces or heels of the screw 140 corresponding to the flutes 138, the flutes are radiused at 0.312 inches centered on a perpendicular to the tip of screw 140. As known to those skilled in the art, flutes are longitudinal channels formed in a tap to create cutting edges on the thread profile and to provide chip spaces and cutting fluid passages. The cutting face of the flutes may possess positive, negative, or zero rake, in accord with a desired angular relationship between the cutting face with a radial line through the crest of the tooth at the cutting edge. In this aspect of the invention, two flutes 138 are formed opposite one another as shown in FIG. 12B. As shown in FIG. 12A, The interior depth of the hollow head 135 is 0.154 inches. A recessed threaded portion 136, having a maximum depth of about 0.11 inches, is provided at a central portion of a bottom of the hollow head 135. In one aspect, recessed threaded portion 136, as shown in FIG. 12C, has a thread depth of about 0.07 inches with a thread diameter of about 0.0595 inches. The overall depth of the threaded portion 136 is about 0.11 inches. The terminus of the recessed threaded portion 136 may comprise a chamfered portion, as illustrated. Torque transmitting structures 180 are also provided at a bottom of the hollow head 135 to facilitate mechanical securement of the screw 140 into a receiving surface, such as a bone. The torque transmitting structures 180 illustrated in FIG. 12C comprise 0.040 inch deep holes having a diameter of about 0.049 inches (±0.0005) spaced on a diameter of the screw hollow head 135 of 0.161 inches (+0.0005).

Figure 12E:
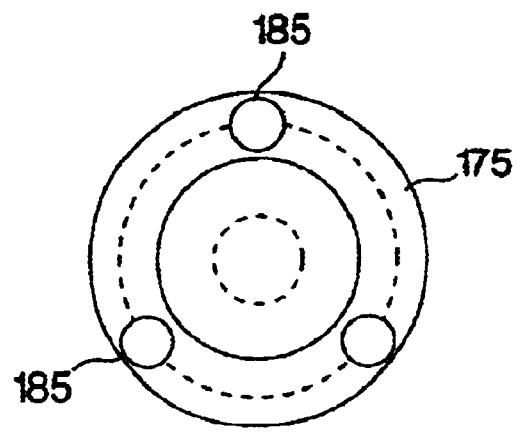
Figure 12F:
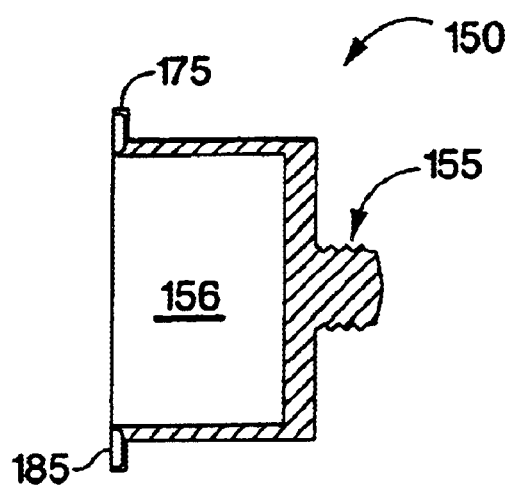

FIGS. 12E–12F illustrate an embodiment of a sustained release holding device 150 configured for insertion into the hollow head 135 of screw 140. A threaded shank 155 is disposed at a bottom portion of the sustained release holding device 150. Threaded shank 155 is configured to matingly engage the opening formed by the recessed threaded portion 136 of screw 140. As shown in FIG. 12F, the threaded shank 155 has a total axial length of about 0.065 inches, of which the threads comprise about 0.06 inches to engage a corresponding portion of threaded portion 136 of screw 140.

An outer diameter of the sustained release holding device 150 of FIGS. 12E–12F is 0.236 inches and the depth of an interior cavity 156 defined thereby is approximately 0.175 inches. The inner diameter of the sustained release holding device 150 is 0.183 inches. At an upper portion thereof is a lip 175 having an outer diameter of 0.295 inches configured to matingly engage the lip 137 of the hollow head 135 of screw 140. Torque transmitting structures 185 are provided in lip 175 of the sustained release holding device 150 to facilitate mechanical securement of the sustained release holding device 150 into the hollow head 135 of screw 140. The torque transmitting structures 185 illustrated in FIGS. 12E–12F comprise 0.020 inch deep holes having a diameter of about 0.049 inches,(±0.001) spaced on a diameter of the sustained release holding device 150 lip 175 of 0.239 inches (±0.001).

Figure 13A:
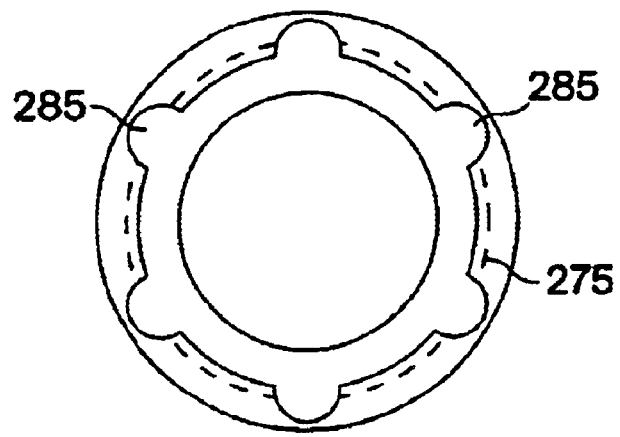
FIGS. 13A–13B depict cross-sectional views of an aspect of a drug delivery system according to another embodiment of the present invention.
Figure 13B:
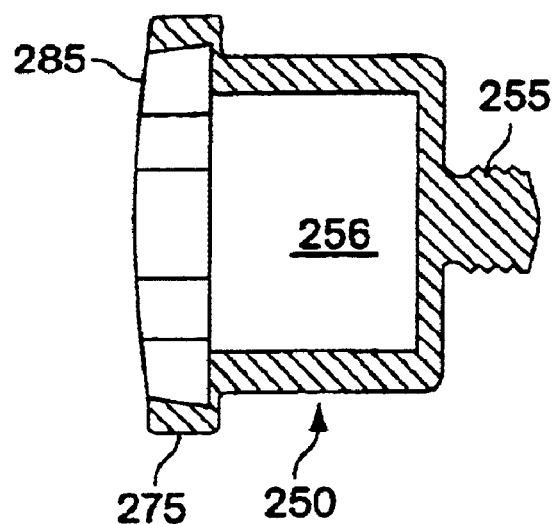

FIGS. 13A–13B illustrate another embodiment of a sustained release holding device 250 configured for insertion into the hollow head 135 of screw 140. A threaded shank 255 is disposed at a bottom portion of the sustained release holding device 250. Threaded shank 255 is configured to matingly engage the opening formed by the recessed threaded portion 136 of screw 140. As shown in FIG. 13B, the threaded shank 255 has a total axial length of about 0.07 inches, of which the threads comprise at least about 0.05 inches to engage a corresponding portion of threaded portion 136 of screw 140.

An outer diameter of the sustained release holding device 250 of FIGS. 13A–13B is 0.236 inches and the depth of the interior cavity 256 defined thereby is approximately 0.154 inches. The inner diameter of the sustained release holding device 250 is 0.183 inches. At an upper portion thereof is a lip 275 having an outer diameter of 0.295 inches configured to matingly engage the lip 137 of the hollow head 135 of screw 140. The upper surfaces of the sustained release holding device 250 are slightly rounded, having a radius of 0.75.

Torque transmitting structures 285 are provided in lip 275 of the sustained release holding device 250 to facilitate mechanical securement of the sustained release holding device 250 into the hollow head 135 of screw 140. The torque transmitting structures 285 illustrated in FIG. 13A comprise recessed portions in the sidewall of the lip 275 that are approximately 0.06 inches deep. As shown, these recessed portions are configured to extend slightly inwardly with increasing depth, at an angle of between approximately 8°–12°. The torque transmitting structures or recessed portions 285 are, as illustrated, generally semi-circular, possessing a diameter of about 0.049 inches (±0.001) spaced on a diameter of the sustained release holding device 250 lip 275 of 0.239 inches (±0.001). Spacing and geometry of the torque transmitting structures or recessed portions 285 may be freely varied to suit the tools and fittings available to produce the torque required to secure the sustained release holding device within the hollow head 135 of screw 140 and may comprise, for example, slots, keys or holes.

Figure 14A:
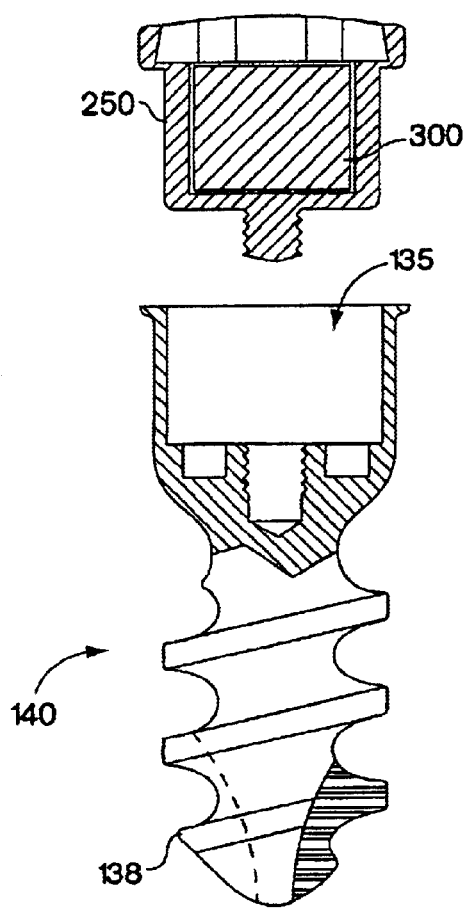
Figure 14B:
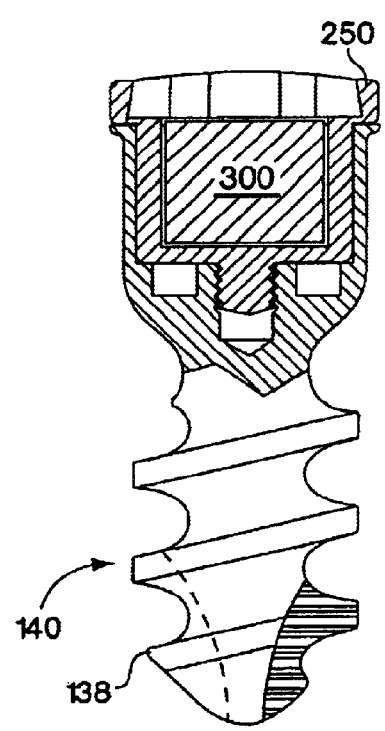
Figure 14C:
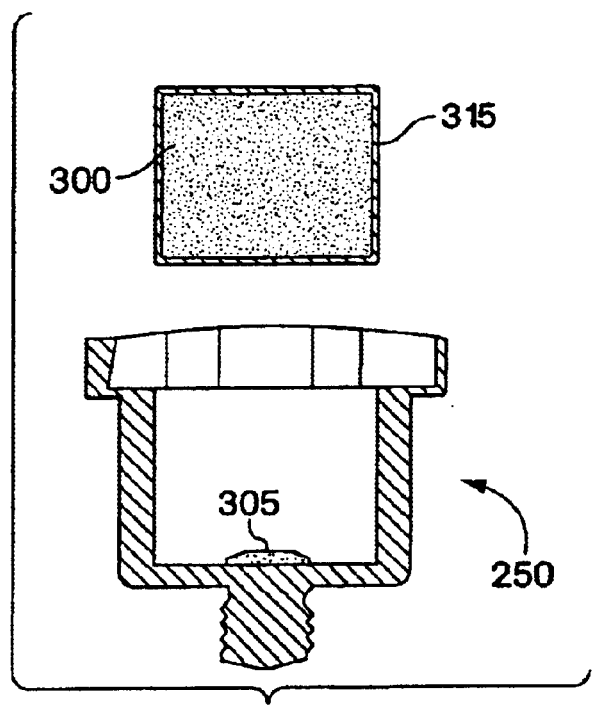

The assembled structure of sustained release holding device 250 and the hollow head 135 of screw 140 is depicted in FIGS. 14A–14B, wherein a drug payload 300 is shown within the sustained release holding device 250. FIG. 14C shows, one means of insertion and securement of the drug payload 300 within the sustained release holding device 250. An adhesive 305 is provided along one or more inner surfaces of the sustained release holding device 250 prior to insertion of the drug payload 300. Upon insertion of the drug payload 300, the adhesive 305 sets and retains the drug payload in place. Although it is preferred that the adhesive 305 have a low enough viscosity to permit the adhesive to flow into gaps between the drug payload 300 and the inner surfaces of sustained release holding device 250, this property is not required and any adhesive 305 compatible with the drug payload coating layer or rate-limiting barrier 315, the drug itself, and/or the material of the sustained release holding device 250, corresponding to various embodiments of the invention, is acceptable.

In accord with the invention, the adhesive 305 may be one that can be applied, at room temperature, by a physician, veterinarian, or medical worker, in accord with the application to facilitate flexibility of drug payload 300 selection and application. It is also possible, in accord with the invention, to pre-form frequently applied drug payloads 300 within the sustained release holding device 250 to simplify ease of end use by a physician, veterinarian, or medical worker. Such pre-formed combinations of drug payload 300 and screw 140 could additionally permit utilization of other means of adhesive affixation, including thermosetting resins or compounds. However, any adhesive process utilizing elevated temperatures would have to be selected so as not to materially degrade either the coating of the drug payload 300 or the drug contained therein, as the efficacy of various drugs have been shown to be adversely affected by elevated temperatures. Further, such pre-formed combinations of drug payloads 300 and screw 140 would require some adjustment to the structures and methods provided herein to permit the screw 140 to be inserted into the target substrate (e.g., bone) by application of torque directly to the head or upper portion of the screw or of an upper portion of the sustained release holding device (e.g., 250). In other words, torque transmitting structures 285 can be disposed within or integrated into the head or upper portion of the screw 140 or sustained release holding device 250 in a manner known to those skilled in the art.

Figure 14D:
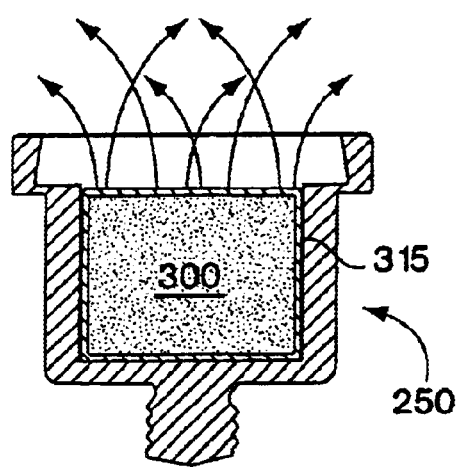

Once implanted, the drug payload 300 is released at a controlled rate over an extended period of time, in accord with the intended therapeutic result, into the area of the patient's body surrounding the insertion site as represented in FIG. 14D. The release rate may be controlled, for example, by appropriate variance of coating layer or rate-limiting barrier 315 properties and geometry. The coating layer 315, such as but not limited to a polymer coating layer, may be selectively omitted, entirely or partially, from one or more portions of the surface area of the drug to be delivered, particularly from the drug surface adjacent the outlet of the sustained release holding device 250. In one aspect thereof, the coating layer 315 may be applied only to a surface of the drug payload 300 adjacent the opening of the sustained release holding device 250. In such an embodiment, adhesive 305 should be selected so as not to structurally or chemically degrade the drug(s) present in the drug payload 300.

In still another aspect thereof, the coating layer 315 may be applied to a surface of the drug payload 300 adjacent the opening of the sustained-release holding device 250 and to an opposing surface adjacent adhesive 305, wherein the adhesive is selected by volume and/or viscosity to limit flow of the adhesive to adjoining surfaces of the drug payload not having a coating layer.

One device suitable for use in installing an embodiment of the drug delivery system of the invention is depicted in FIGS. 15A–15B. The drill imparting the torque to the screw may comprise essentially any automated, motorized, or manual drill considered acceptable by medical practitioners for medical applications. In one aspect of contemplated surgical procedures, the area of implantation is made accessible by movement of soft tissues away from the targeted area and a conventional hand held drill may be used. In other aspects thereof, to minimize trauma to the tissues, less invasive procedures are used and the drill bit 405 may be advantageously provided within a cannula or drill sleeve, such as those conventionally applied during arthroscopic or orthroscopic surgery, to prevent damage to soft tissue during drilling.

FIGS. 15A–15B illustrate different embodiments of drivers 450 configured to drive screw 140 into the preformed pilot holes 410, 420 as discussed later with respect to FIG. 16A. Each driver 450 has a head 460 configured to matingly engage torque transmitting structures 180 on the interior portion of hollow head 135. As depicted in FIGS. 15A–15B, the head 460 comprises three drive members 465 approximately 0.040 inches in length having a diameter of about 0.049 inches spaced on a diameter of 0.161 inches to correspond with the screw 140 depicted in FIGS. 12A–12F. The drive members 465 can assume any shape, number or distribution corresponding to that of the torque transmitting structures 180 of the hollow head 135. In operation, the drive shaft 470 of the driver 450 is rotated clockwise or counterclockwise, at a proximal end, to produce a corresponding clockwise or counterclockwise motion of the head 460 at a distal end. The proximal end of the driver 450 may, as shown in FIG. 15A have a knob 475 having a radius configured to permit generation of varying degrees of torque in accord with a moment arm applied by a medical provider's digital manipulation. Alternatively, as shown in FIG. 15B, the drive shaft itself may simply be provided with a high friction or grippable surface 480 having a diameter substantially equal to the diameter of the drive shaft 470 itself to permit less torque than the driver 450 depicted in FIG. 15A to thereby enable a finer degree of control and tactile sensitivity. Although the drivers 450 depicted are manually operated, the drivers 450 may advantageously be motorized.

A method for implanting a drug delivery device in accord with FIGS. 14A–14D into a bone is depicted in FIGS. 16A–16G.

Figure 16A:
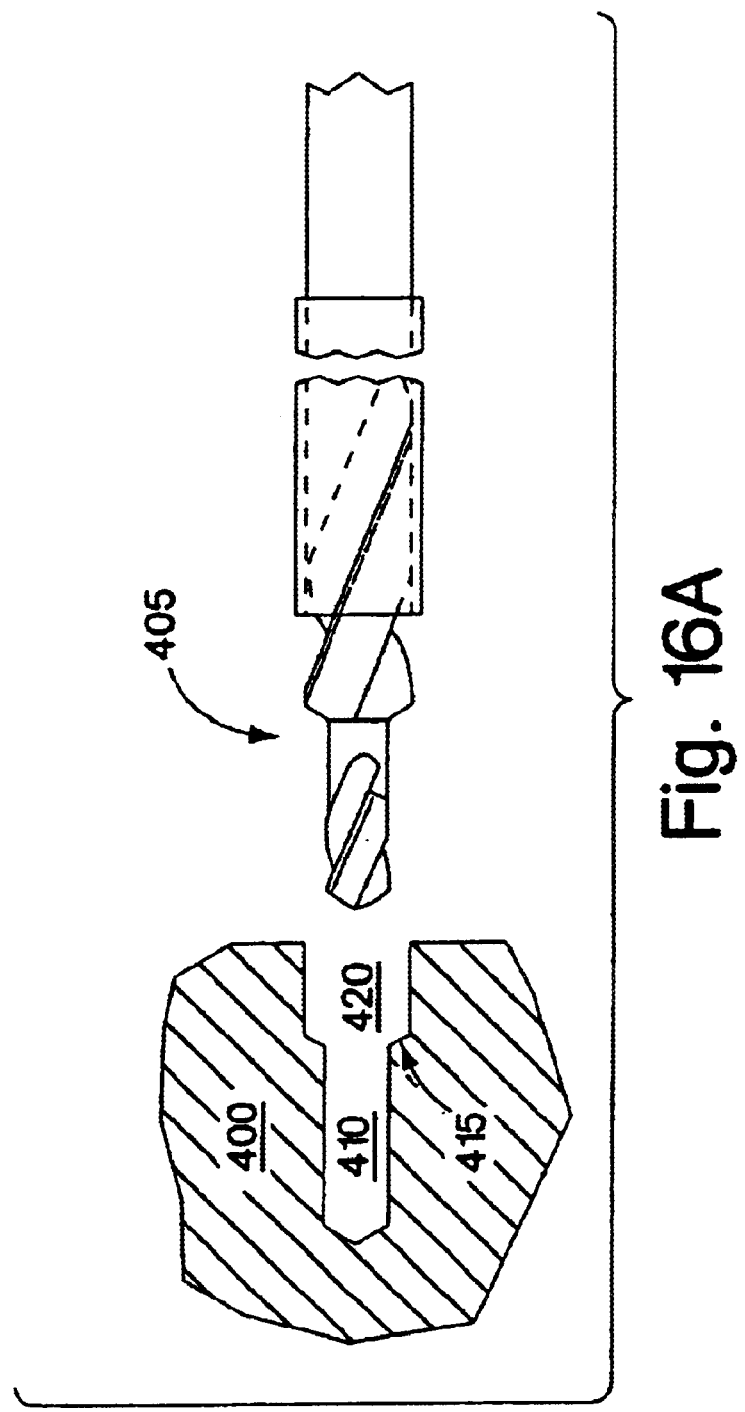

First, as shown in FIG. 16A, it is preferred to drill a pilot hole into the bone 400. Alternatively, a self-tapping or self-drilling screw may be used. The drill bit 405 depicted in FIG. 16A produces a first pilot hole 410 having a first depth and first diameter D1 and a second pilot hole 420 having a second depth and a second diameter D2. The first diameter D1 is selected to less than the outer diameter of the threaded shank 132 (i.e., less than 0.25 inches in the embodiment of FIG. 12A) and is preferably less than or equal to the root diameter of the threaded shank 132 (i.e., less than 0.135 inches in the embodiment of FIG. 12A) or of the tip of the screw 140 (i.e., less than the initial root diameter of about 0.125 inches in the embodiment of FIG. 12A) to permit effective securement of the threaded shank 132 into the bone 400.

An intermediary portion 415 between the first diameter and the second diameter is preferably chamfered or angled to correspond to the shape of the shoulder 134 of the screw 140. An abrupt step-change in diameter may, however, also be used in accord with a screw so configured in accord with the invention. Second diameter D2 of pilot hole 420 is configured to substantially correspond to an outer diameter of the hollow head 135 of the screw 140. Although not shown, drill bit 405 may comprise a third section configured to drill a relatively shallow third hole having a thickness corresponding to a thickness of the lip 137 of the hollow head 135. In this way, an upper edge of the lip and hollow head may be provided flush with the surface of the bone.

Figure 16B:
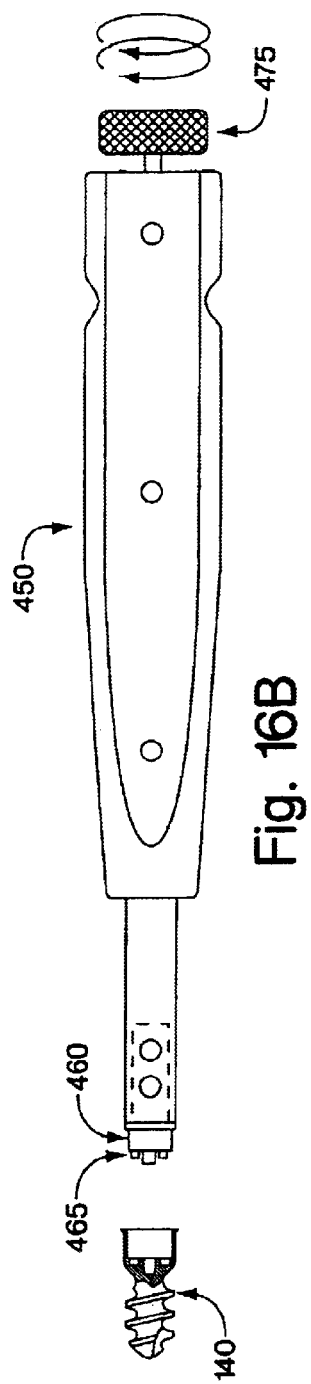
Figure 16C:
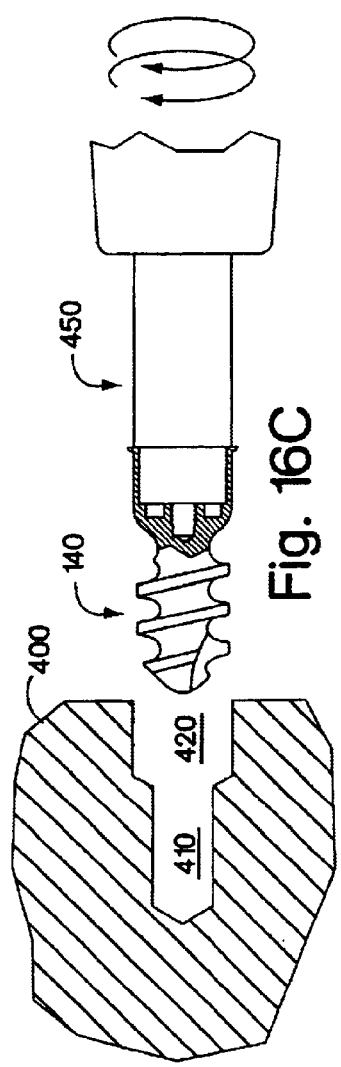
Figure 16D:
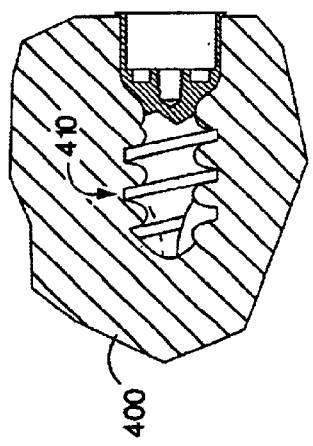

FIG. 16B illustrates a step of connecting the screw 140 of FIG. 12A and the driver 450 of FIG. 15A in accord with the invention. FIG. 16C illustrates insertion of the screw 140 into the pilot holes 410, 420 drilled into the bone 400 by applying a torque to the driver 450 drive shaft 470 by means of the knob 475. FIG. 16D depicts the screw 140 inserted into the bone 400.

Following insertion of the screw 140, the drug payload 300 is inserted in accord with the aspect of the invention depicted in FIG. 14C, wherein a health care provider first places an adhesive material 305 on at least one surface of the inner walls of the sustained release holding device (e.g., 250) and, second, presses the drug payload against the adhesive to secure the drug payload within the sustained release holding device.

Once the drug payload 300 is secured within the sustained release holding device 250 and following lapse of a setting time for the adhesive, if necessary, the sustained release holding device 250 may be inserted into the hollow head 135 of screw 140, as shown in FIGS. 16E–16C. FIG. 16E illustrates a step of connecting the sustained release holding device 250 of FIGS. 13A–13B and a driver 550 substantially similar to that of driver 450 FIG. 15A. In this particular embodiment of driver 550, the distal end 590 has a raised portion or boss 555 configured to engage the inside of lip 275 of the sustained release holding device 250. This engagement is accomplished by rotating knob 575 clockwise to retract the drive shaft 570 linearly away from distal end 590 using threads 580 to convert the rotary motion to a linear motion.

The inner diameter ID of distal end 590 between points A1 and A2, as depicted in FIG. 16F, is substantially constant and is greater than an outside diameter OD of the driver head 560. The inner diameter ID of distal end 590 at point A2 is substantially equal to an outside diameter OD of the driver head 560. The inner diameter ID of distal end 590 between points A2 and A3, as depicted in FIG. 16F, decreases with increasing, distance from the front or leftmost of distal end, as shown, and is less than an outside diameter OD of the driver head 560. Therefore, as the driver head 560 is withdrawn past point A2, the driver head exerts an outward force against the inner walls of the distal end 590. The narrowed portion 585 adjacent the distal end 590 facilitates outward flexure of the distal end walls, including the raised portion or boss 555.

Accordingly, when driver head 560 is retracted, boss 555 is splayed outwardly to engage the inside of lip 275 of the sustained release holding device 250 and secure the sustained release holding device to the driver 550 as shown in FIG. 16F. Once secured, the sustained release holding device 250 is placed within the hollow head so that the threaded shank 225 is adjacent to and in initial contact with the threaded portion 136. Driver 550 is then itself rotated clockwise to screw the threaded shank 225 into the threaded portion 136 to secure the sustained release holding device 250 in the hollow head 135.

Engagement between the boss 555 and the lip 275 of sustained release holding device 250 is then released by rotating knob 575 to linearly advance driver head 560 and return the outwardly splayed boss 555 to its original or equilibrium position, whereupon it does not contact the lip 275. The driver 550 may then be removed, leaving the installed bone screw 140 bearing a drug payload 300 in sustained release holding device 250, as shown in FIG. 16G.

While several embodiments of a sustained release device, as deployed in a bone screw, have been described in detail, it will be appreciated that the general principle of configuring orthopedic hardware as a platform for a drug delivery system may be readily adapted, with little experimentation, to a large number of orthopedic hardware components.

For example, orthopedic hardware components include staples, tacks, darts, a variety of screws including cannulated bone screws and interference bone screws, bolts, washers FIG., plates FIG., pins such as those driven into or through bones, buttons, staples, and wires. These components serve different purposes, and are used variously in different parts of the anatomy. Any of these components may serve as an anchor to which a drug delivery system may be associated, either removably or permanently, so that a compound may be released over an extended time near the site of the component. Similarly, a prosthetic joint or a component of a prosthetic joint may have a sustained delivery system attached thereto. A wide range of suitable orthopedic hardware is known in the art, and is described for example in several well-established orthopedic texts, including Campbell's Operative Orthopaedics, $9^{th}$ Ed., S. Canale, K. Daugherty and L. Jones (Editors) (1993 Mosby-Year Book), Surgery of the Foot and Ankle, $7^{th}$ Ed., M. Coughlin and R. Mann (Editors) (1999 Mosby-Year Book), The Shoulder, $2^{nd}$ Ed., C. Rockwood, F. Matsen, M. Wirth, and L. Reines (Editors) (1998 WB Saunders Co.), Ao/Asif instruments and implants A Technical Manual, $2^{nd}$ Ed., R. Texhammar and C. Colton (1994 Springer Verlag), and Manual of Arthroscopic Surgery, M. Strobel (2001 Springer Verlag). The teachings of these texts are incorporated herein by reference.

Similarly, a number of different techniques may be used to permanently or temporarily associate or couple the sustained release device to the orthopedic hardware component. For example, a number of threaded techniques are described above. These techniques may be readily adapted to a number of rotatably attachable and detachable sustained release device configurations that thread onto the component as a cap (e.g., about a threaded protrusion on the component having outwardly projecting threads), or into the component (e.g., into a threaded recession within the component having inwardly directed threads). Other arrangements may be used, such as a cylindrical sustained release device with a hole through its central axis, such that it may be fastened with a bolt to a suitably threaded orthopedic hardware component. Other turning and locking configurations are known in the mechanical arts, and may be readily adapted to the systems herein. Similarly, any number of interference fits, e.g., fits in which one piece is frictionally engaged to another, may be used. Similarly, a looser fit may be combined with a wedge or pin that is driven into the sustained device to expand the device so that it engages the walls of a suitably fashioned cavity in the orthopedic hardware component.

As further examples, a suture eye may be affixed to the sustained release device and the orthopedic hardware component. The sustained release device may then be readily attached to the component with a suture between the respective eyes. This technique may be combined with a mechanical fit for the sustained release device to the component to provide for convenient exchange of one sustained release device for another.

Where there is no anticipated need to remove the sustained release device from the orthopedic hardware component, as would otherwise be used to replace or modify a dosage for a compound, other configurations may be employed. Any suitable cavity may be provided within an orthopedic hardware component to receive a high-solubility (or simply "soluble") or low-solubility sustained release device, such as the devices described above. In certain embodiments of a low-solubility sustained release device in a rigid matrix, the device may simply comprise a tablet embedded within, or affixed to the surface of, the orthopedic hardware component. More generally, the sustained release device may be integrally formed in the orthopedic hardware component so that no separate attachment of the sustained release device is required when the component is implanted into a body.

Additionally, it should be appreciated that any number of compounds may be delivered through the systems described herein, either for treatment of a surgical site associated with the orthopedic hardware, or for any other treatment suitably administered near the hardware. This further contemplates placement of orthopedic hardware, such as a pin or screw, exclusively to serve as an anchor for the drug delivery system.

In certain embodiments, as described in varying detail above, useful compounds may include steroids, antibiotics, anti-inflammatory drugs, anti-proliferative compounds, antimyotic compounds, an antimitotic compounds, antimetabolite compounds, pain-relieving drugs, corticosteroids, angiostatic steroids, non-steroidal anti-inflammatory agents, and/or co-drugs.

In certain embodiments, as described above in varying detail, compounds may include compounds having a variety of useful therapeutic effects, including anti-inflammatory effects, pain-relief effects, anesthetic effects, immune suppressant effects, antibiotic effects, anti-viral effects, cancer-fighting effects, anti-cancer effects, anti-proliferative effects, cartilage-protecting effects, or an anti-scarring effects.

The purpose of the above description and examples is to illustrate some embodiments of the present invention without implying any limitation. It will be apparent to those of skill in the art that various modifications and variations may be made to the method and device of the present invention without departing from the spirit or scope of the invention. All patents and publications cited herein are incorporated by reference in their entireties.

What is claimed is:

1. A system comprising:
    a bone screw attachable to a portion of a body, the bone screw including a head; and
    a sustained release device formed in a chamber in the head, the sustained release device configured to release a compound having a therapeutic effect over an extended period of time.

2. The system of claim 1 wherein the bone screw is at least one of a cannulated bone screw and an interference bone screw.

3. A system comprising:
    an orthopedic hardware component attachable to a portion of a body; and
    a sustained release device threaded to the orthopedic hardware component such that the sustained release device is rotatable removable from and replaceable to the orthopedic hardware component, the sustained release device configured to release a compound having a therapeutic effect over an extended period of time.

4. The system of claim 3 wherein the sustained release device is a cap threaded to an outward projecting surface of the orthopedic hardware component.

5. The system of claim 3 wherein the sustained release device is a screw threaded to an inwardly projecting surface of the orthopedic hardware component.

6. A system comprising:
    an orthopedic hardware component attachable to a portion of a body; and
    a sustained release device removably associated with the orthopedic hardware component using an interference fit, the sustained release device configured to release a compound having a therapeutic effect over an extended period of time.

7. A system comprising:
an orthopedic hardware component attachable to a portion of a body and including a first suture eve; and
a sustained release device including a second suture eye, the sustained release device removably associated with the orthopedic hardware component using a suture through each of the first suture eye and the second suture eye, the sustained release device configured to release a compound having a therapeutic effect over an extended period of time.

8. The system of claim 6 or 7, the orthopedic hardware component including a chamber, the sustained release device configured for placement in the chamber of the orthopedic hardware component.

9. A system comprising:
an orthopedic hardware component attachable to a portion of a body; and
a sustained release device associated with the orthopedic hardware component, the sustained release device configured to release a compound having a therapeutic effect over an extended period of time wherein the compound is a low-solubility compound.

10. The system of claim 9 wherein the compound comprises a matrix of an effective agent and a polymer that is permeable to the effective agent.

11. The system of claim 9 wherein the sustained release device includes an inner core containing the compound, the sustained release device further comprising a non-bioerodible polymer coating layer, the non-bioerodible polymer coating layer being permeable to the compound, wherein the non-bioerodible polymer coating layer covers the inner core and is essentially non-release rate limiting.

12. A system comprising:
an orthopedic hardware component attachable to a portion of a body; and
a sustained release device associated with the orthopedic hardware component, the sustained release device configured to release a compound having a therapeutic effect over an extended period of time wherein the compound comprises a soluble compound.

13. The system of claim 12 wherein the compound is surrounded by an outer layer that covers the compound and includes a first surface and a second surface, the first surface being substantially impermeable to the compound and the second surface being permeable to the compound and limiting a release rate of the compound.

14. The system of claim 1, the compound including at least one of a steroid, an antibiotic, an anti-inflammatory drug, an antiproliferative compound, an antimyotic compound, an antimitotic compound, an antimetabolite compound, a pain-relieving drug, a corticosteroid, an angiostatic steroid, a non-steroidal anti-inflammatory agent, or a co-drug.

15. The system of claim 1, the therapeutic effect including at least one of an anti-inflammatory effect, a pain-relief effect, an anesthetic effect, an immune suppressant effect, an antibiotic effect, an anti-viral effect, a cancer-fighting effect, an anti-cancer effect, an anti-proliferative effect, a cartilage-protecting effect, or an anti-scarring effect.

16. A method comprising:
attaching an orthopedic hardware component to a portion of a body wherein attaching the orthopedic hardware component further comprises driving a pin into a bone of the body;
providing a compound having a therapeutic effect;
associating the compound with the orthopedic hardware component; and
releasing the compound over an extended period of time.

17. A method comprising:
attaching an orthopedic hardware component to a portion of a body wherein attaching the orthopedic hardware component further comprises suturing the component to a soft tissue of the body;
providing a compound having a therapeutic effect;
associating the compound with the orthopedic hardware component; and
releasing the compound over an extended period of time.

18. A method comprising:
attaching an orthopedic hardware component to a portion of a body wherein the orthopedic hardware component includes at least one of a staple, a tack, a dart, a bolt, a washer, a plate, a prosthetic joint, a component of a prosthetic joint, an anchor, a pin, a wire, or a button;
providing a compound having a therapeutic effect;
associating the compound with the orthopedic hardware component; and
releasing the compound over an extended period of time.

19. A method comprising:
attaching an orthopedic hardware component to a portion of a body;
providing a compound having a therapeutic effect;
associating the compound with the orthopedic hardware component wherein associating the compound with the orthopedic hardware component further comprises removably attaching a sustained release device that includes the compound to the orthopedic hardware component using at least one of threads that rotatably engage the sustained release device to the orthopedic hardware component, an interference fit between the sustained release device and the orthopedic hardware component, a pin passing through the orthopedic hardware component and the sustained release device, or a suture passing between a suture eye of each one of the orthopedic hardware component and the sustained release device; and
releasing the compound over an extended period of time.

20. The method of claim 16 wherein the compound is a low-solubility compound, releasing the compound further comprising exposing the compound to a bodily fluid such that the compound dissolves into the bodily fluid.

21. The method of claim 16 wherein the compound is a high-solubility compound, releasing the compound further comprising exposing the compound to a bodily fluid through a membrane that limits a rate of release of the compound.

22. The method of claim 16 wherein the compound includes at least one of a steroid, an antibiotic, an anti-inflammatory drug, an antiproliferative compound, an antimyotic compound, an antimitotic compound, an antimetabolite compound, a pain-relieving drug, a corticosteroid, an angiostatic steroid, a non-steroidal anti-inflammatory agent, or a co-drug.

23. The method of claim 16 wherein the therapeutic effect includes at least one of an anti-inflammatory effect, a pain-relief effect, an anesthetic effect, an immune suppressant effect, an antibiotic effect, an anti-viral effect, a cancer-fighting effect, an anti-cancer effect, an anti-proliferative effect, a cartilage-protecting effect, or an anti-scarring effect.

24. The method of claim 16 wherein attaching the orthopedic hardware component comprises attaching the component within a synovial capsule of a joint, the compound including one or more treatments for at least one of osteoarthritis or rheumatoid arthritis.

25. The method of claim 17 wherein the compound is a low-solubility compound, releasing the compound further comprising exposing the compound to a bodily fluid such that the compound dissolves into the bodily fluid.

26. The method of claim 17 wherein the compound is a high-solubility compound, releasing the compound further comprising exposing the compound to a bodily fluid through a membrane that limits a rate of release of the compound.

27. The method of claim 17 wherein the compound includes at least one of a steroid, an antibiotic, an anti-inflammatory drug, an antiproliferative compound, an antimyotic compound, an antimitotic compound, an antimetabolite compound, a pain-relieving drug, a corticosteroid, an angiostatic steroid, a non-steroidal anti-inflammatory agent, or a co-drug.

28. The method of claim 17 wherein the therapeutic effect includes at least one of an anti-inflammatory effect, a pain-relief effect, an anesthetic effect, an immune suppressant effect, an antibiotic effect, an anti-viral effect, a cancer-fighting effect, an anti-cancer effect, an anti-proliferative effect, a cartilage-protecting effect, or an anti-scarring effect.

29. The method of claim 17 wherein attaching the orthopedic hardware component comprises attaching the component within a synovial capsule of a joint, the compound including one or more treatments for at least one of osteoarthritis or rheumatoid arthritis.

30. The method of claim 18 wherein the compound is a low-solubility compound, releasing the compound further comprising exposing the compound to a bodily fluid such that the compound dissolves into the bodily fluid.

31. The method of claim 18 wherein the compound is a high-solubility compound, releasing the compound further comprising exposing the compound to a bodily fluid through a membrane that limits a rate of release of the compound.

32. The method of claim 18 wherein the compound includes at least one of a steroid, an antibiotic, an anti-inflammatory drug, an antiproliferative compound, an antimyotic compound, an antimitotic compound, an antimetabolite compound, a pain-relieving drug, a corticosteroid, an angiostatic steroid, a non-steroidal anti-inflammatory agent, or a co-drug.

33. The method of claim 18 wherein the therapeutic effect includes at least one of an anti-inflammatory effect, a pain-relief effect, an anesthetic effect, an immune suppressant effect, an antibiotic effect, an anti-viral effect, a cancer-fighting effect, an anti-cancer effect, an anti-proliferative effect, a cartilage-protecting effect, or an anti-scarring effect.

34. The method of claim 18 wherein attaching the orthopedic hardware component comprises attaching the component within a synovial capsule of a joint, the compound including one or more treatments for at least one of osteoarthritis or rheumatoid arthritis.

35. The method of claim 19 wherein the compound is a low-solubility compound, releasing the compound further comprising exposing the compound to a bodily fluid such that the compound dissolves into the bodily fluid.

36. The method of claim 19 wherein the compound is a high-solubility compound, releasing the compound further comprising exposing the compound to a bodily fluid through a membrane that limits a rate of release of the compound.

37. The method of claim 19 wherein the compound includes at least one of a steroid, an antibiotic, an anti-inflammatory drug, an antiproliferative compound, an antimyotic compound, an antimitotic compound, an antimetabolite compound, a pain-relieving drug, a corticosteroid, an angiostatic steroid, a non-steroidal anti-inflammatory agent, or a co-drug.

38. The method of claim 19 wherein the therapeutic effect includes at least one of an anti-inflammatory effect, a pain-relief effect, an anesthetic effect, an immune suppressant effect, an antibiotic effect, an anti-viral effect, a cancer-fighting effect, an anti-cancer effect, an anti-proliferative effect, a cartilage-protecting effect, or an anti-scarring effect.

39. The method of claim 19 wherein attaching the orthopedic hardware component comprises attaching the component within a synovial capsule of a joint, the compound including one or more treatments for at least one of osteoarthritis or rheumatoid arthritis.

\* \* \* \* \*